US009526526B2

(12) United States Patent
Zhang et al.

(10) Patent No.: US 9,526,526 B2
(45) Date of Patent: Dec. 27, 2016

(54) PEDICLE SCREW

(71) Applicant: GLOBUS MEDICAL, INC., Audubon, PA (US)

(72) Inventors: Hong Zhang, Plano, TX (US); Dan Sucato, Dallas, TX (US)

(73) Assignee: GLOBUS MEDICAL, INC., Audubon, PA (US)

( * ) Notice: Subject to any disclaimer, the term of this patent is extended or adjusted under 35 U.S.C. 154(b) by 47 days.

(21) Appl. No.: 14/699,937

(22) Filed: Apr. 29, 2015

(65) Prior Publication Data

US 2015/0257791 A1 Sep. 17, 2015

Related U.S. Application Data

(63) Continuation of application No. 12/364,423, filed on Feb. 2, 2009, now Pat. No. 9,050,141.
(Continued)

(51) Int. Cl.
A61B 17/70 (2006.01)
A61B 17/86 (2006.01)
A61B 17/56 (2006.01)

(52) U.S. Cl.
CPC ......... A61B 17/7034 (2013.01); A61B 17/705 (2013.01); A61B 17/7079 (2013.01);
(Continued)

(58) Field of Classification Search
CPC ............ A61B 17/7001; A61B 17/7032; A61B 17/7034; A61B 17/7035; A61B 17/7037; A61B 17/7038; A61B 17/704; A61B 17/7041; A61B 17/7046
See application file for complete search history.

(56) References Cited

U.S. PATENT DOCUMENTS 4,653,489 A 3/1987 Tronzo
4,743,260 A 5/1988 Burton
(Continued)

FOREIGN PATENT DOCUMENTS

JP 2003250822 A 9/2003
WO 2008128105 A1 10/2008
(Continued)

OTHER PUBLICATIONS

Berguiristain, J. L., et al., "Experimental Scoliosis by Epiphysiodesis in Pigs," International Orthopaedics (1980), 3:317-321.
(Continued)

Primary Examiner — Lynnsy Summitt

(57) ABSTRACT

The present invention includes a pedicle screw made with a bone fastener and a rod coupling head, the rod coupling head comprising an upper rod coupling: the lower rod coupling having a lateral rod opening adapted to receive a permanent rod; an angled bore extends into the lateral rod opening; and a permanent rod fastener in the angled bore to engage a permanent rod in the lateral rod opening; and a upper rod coupling having an upper rod opening adapted to receive a temporary rod, wherein the upper rod opening is formed to receive a temporary rod fastener; wherein the upper rod coupling is detachable from the lower rod coupling at a transition and a temporary rod is temporarily affixed into the upper rod opening during a bone realignment and a permanent rod is positioned in the lateral rod opening and engaged by the permanent rod fastener upon final bone alignment.

24 Claims, 16 Drawing Sheets

Related U.S. Application Data

(60) Provisional application No. 61/025,760, filed on Feb. 2, 2008, provisional application No. 61/080,150, filed on Jul. 11, 2008.

(52) U.S. Cl.
CPC ...... *A61B 17/8685* (2013.01); *A61B 17/7052* (2013.01); *A61B 2017/564* (2013.01)

(56) References Cited

U.S. PATENT DOCUMENTS

| | | | |
|---|---|---|---|
| 4,772,261 A | 9/1988 | Von Hoff et al. | |
| 4,946,458 A | 8/1990 | Harms et al. | |
| 5,005,562 A | 4/1991 | Cotrel | |
| 5,047,030 A | 9/1991 | Draenert | |
| 5,067,955 A | 11/1991 | Cotrel | |
| 5,129,349 A | 7/1992 | Glen | |
| 5,133,717 A | 7/1992 | Chopin | |
| 5,219,349 A | 6/1993 | Krag et al. | |
| 5,329,933 A | 7/1994 | Graf | |
| 5,385,565 A | 1/1995 | Ray | |
| 5,397,363 A | 3/1995 | Gelbard | |
| 5,620,443 A | 4/1997 | Gertzbein et al. | |
| 5,630,816 A | 5/1997 | Kambin | |
| 5,702,395 A | 12/1997 | Hopf | |
| 5,707,372 A | 1/1998 | Errico et al. | |
| 5,728,097 A | 3/1998 | Mathews | |
| 5,800,407 A | 9/1998 | Eldor | |
| 5,871,484 A | 2/1999 | Spievack et al. | |
| 5,876,403 A | 3/1999 | Shitoto | |
| 5,993,449 A | 11/1999 | Schlapfer et al. | |
| 6,077,263 A * | 6/2000 | Ameil | A61B 17/7032 606/276 |
| 6,090,113 A | 7/2000 | Le Couedic et al. | |
| 6,136,002 A | 10/2000 | Shih et al. | |
| 6,214,012 B1 | 4/2001 | Karpman et al. | |
| 6,248,106 B1 | 6/2001 | Ferree | |
| 6,287,309 B1 | 9/2001 | Baccelli et al. | |
| 6,423,062 B2 | 7/2002 | Enayati | |
| 6,461,359 B1 | 10/2002 | Tribus et al. | |
| 6,488,681 B2 | 12/2002 | Martin et al. | |
| 6,517,542 B1 | 2/2003 | Papay et al. | |
| 6,554,830 B1 | 4/2003 | Chappius | |
| 6,554,834 B1 | 4/2003 | Crozet et al. | |
| 6,558,390 B2 | 5/2003 | Cragg | |
| 6,565,572 B2 | 5/2003 | Chappius | |
| 6,569,164 B1 | 5/2003 | Assaker et al. | |
| 6,582,439 B1 | 6/2003 | Sproul | |
| 6,610,063 B2 | 8/2003 | Kumar et al. | |
| 6,620,195 B2 | 9/2003 | Goble et al. | |
| 6,623,485 B2 | 9/2003 | Doubler et al. | |
| 6,663,637 B2 | 12/2003 | Dixon et al. | |
| 6,730,095 B2 | 5/2004 | Olson, Jr. et al. | |
| 6,740,086 B2 | 5/2004 | Richelsoph | |
| 6,740,090 B1 | 5/2004 | Cragg et al. | |
| 6,749,613 B1 | 6/2004 | Conchy et al. | |
| 6,755,835 B2 | 6/2004 | Schultheiss et al. | |
| 6,780,191 B2 | 8/2004 | Sproul | |
| 6,858,030 B2 | 2/2005 | Martin et al. | |
| 6,881,215 B2 | 4/2005 | Assaker et al. | |
| 6,899,714 B2 | 5/2005 | Vaughan | |
| 6,942,698 B1 | 9/2005 | Jackson | |
| 6,945,975 B2 | 9/2005 | Dalton | |
| 6,964,665 B2 | 11/2005 | Thomas et al. | |
| 6,974,460 B2 | 12/2005 | Carbone et al. | |
| 6,976,988 B2 | 12/2005 | Ralph et al. | |
| 6,981,973 B2 | 1/2006 | McKinley | |
| 7,008,433 B2 | 3/2006 | Voellmicke et al. | |
| 7,033,392 B2 | 4/2006 | Schmiel et al. | |
| 7,041,138 B2 | 5/2006 | Lange | |
| 7,163,539 B2 | 1/2007 | Abdelgany et al. | |
| 7,220,262 B1 | 5/2007 | Hynes | |
| 7,658,753 B2 | 2/2010 | Carl et al. | |
| 7,776,072 B2 | 8/2010 | Barry | |
| 7,789,897 B2 | 9/2010 | Sanders | |
| 8,007,522 B2 | 8/2011 | Hutchinson | |
| 8,083,773 B2 | 12/2011 | Durrani | |
| 8,277,453 B2 | 10/2012 | Kave et al. | |
| 2002/0007183 A1 | 1/2002 | Lee et al. | |
| 2002/0013585 A1 | 1/2002 | Gournay et al. | |
| 2002/0095153 A1 | 7/2002 | Jones et al. | |
| 2003/0065329 A1 | 4/2003 | Vaughan | |
| 2003/0144664 A1 | 7/2003 | Cavagna et al. | |
| 2004/0111088 A1* | 6/2004 | Picetti | A61B 17/7001 606/265 |
| 2004/0158247 A1 | 8/2004 | Sitiso et al. | |
| 2005/0203511 A1 | 9/2005 | Wilson-MacDonald et al. | |
| 2005/0234449 A1 | 10/2005 | Aferzon | |
| 2005/0277934 A1* | 12/2005 | Vardiman | A61B 17/7083 606/914 |
| 2006/0036246 A1 | 2/2006 | Carl et al. | |
| 2006/0173456 A1 | 8/2006 | Hawkes et al. | |
| 2006/0195092 A1 | 8/2006 | Barry | |
| 2006/0247623 A1 | 11/2006 | Anderson et al. | |
| 2006/0293659 A1* | 12/2006 | Alvarez | A61B 17/7037 606/305 |
| 2007/0093824 A1* | 4/2007 | Hestad | A61B 17/7032 606/261 |
| 2007/0213715 A1 | 9/2007 | Bridwell et al. | |
| 2007/0213716 A1* | 9/2007 | Lenke | A61B 17/025 606/264 |
| 2007/0225713 A1 | 9/2007 | Altarac et al. | |
| 2007/0233062 A1 | 10/2007 | Berry | |
| 2007/0233089 A1* | 10/2007 | DiPoto | A61B 17/7011 606/279 |
| 2007/0270805 A1 | 11/2007 | Miller et al. | |
| 2007/0270810 A1 | 11/2007 | Sanders | |
| 2007/0286366 A1 | 12/2007 | Deboy et al. | |
| 2008/0027436 A1 | 1/2008 | Cournoyer et al. | |
| 2008/0177323 A1* | 7/2008 | Null | A61B 17/705 606/267 |
| 2008/0255617 A1* | 10/2008 | Cho | A61B 17/702 606/246 |
| 2009/0099605 A1* | 4/2009 | Fallin | A61B 17/7085 606/252 |
| 2009/0131982 A1* | 5/2009 | Schwab | A61B 17/7001 606/246 |
| 2009/0198273 A1 | 8/2009 | Zhang et al. | |
| 2009/0198279 A1 | 8/2009 | Zhang et al. | |
| 2009/0326586 A1 | 12/2009 | Duarte | |
| 2010/0042149 A1 | 2/2010 | Chao et al. | |
| 2010/0076494 A1 | 3/2010 | Markworth | |
| 2010/0247600 A1 | 9/2010 | Xia et al. | |
| 2010/0249843 A1 | 9/2010 | Wegrzyn, III | |
| 2010/0256683 A1 | 10/2010 | Iott et al. | |
| 2011/0137358 A1 | 6/2011 | Manninen | |
| 2012/0221057 A1 | 8/2012 | Zhang et al. | |
| 2013/0090691 A1 | 4/2013 | Zhang et al. | |

FOREIGN PATENT DOCUMENTS

| | | |
|---|---|---|
| WO | 2009097623 A2 | 8/2009 |
| WO | 2009097624 A2 | 8/2009 |

OTHER PUBLICATIONS

Bradford, D.S., et al., "One-stage anterior and posterior hemivertebral resection and arthrodesis for congenital scoliosis." JBJS (1990), 72-A:536-40.

Compere, E.L., et al., "Excision of hemivertebrae for correction of congenital scolioisis: report of two cases." JBJS (1932), 14-A:555-62.

Deviren, V., et al. "Excision of hemivertebrae in the management of congenital scoliosis involving the thoracic and thoracolumbar spine." JBJS (2001), 83-B:496-500.

Floman, Y., et al. "Osteotomy of the fusion mass in scoliosis." JBJS (1982), 64-A:1307-16.

Leatherman, K.D., et al. "Two-stage corrective surgery for congenital deformities of the spine." JBJS (1979), 61-B:324-8.

Suk, S., et al. "Posterior vertebral column resection for severe spinal deformities." Spine (2002), 27:2374-82.

(56) References Cited

OTHER PUBLICATIONS

Suk, S., et al. "Posterior vertebral column resection for severe spinal deformities." Spine (2005), 30:1682-87.
Suk, S., et al. "Posterior vertebral column resection in fixed lumbosacral deformity." Spine (2005), 30:E703-10.
Tokunaga, M., et al. "Verteral decancellation for severe scoliosis." Spine (2000), 25:469-74.
Wiles, P. "Resection of dorsalvertebrae in congenital scoliosis." JBJS (1951), 33-A:151-4.
International Search Report and Written Opinion of KIPO for PCT/US2009/032901 dated Sep. 24, 2009, 12 pages.
International Search Report and Written Opinion of KIPO for PCT/US2009/032899 dated Oct. 15, 2009, 9 pages.
International Search Report and Written Opinion of Australia Patent Office for PCT/US2008/60115 dated Sep. 18, 2008, 9 pages.

* cited by examiner (1) Temporary Rod Insertion

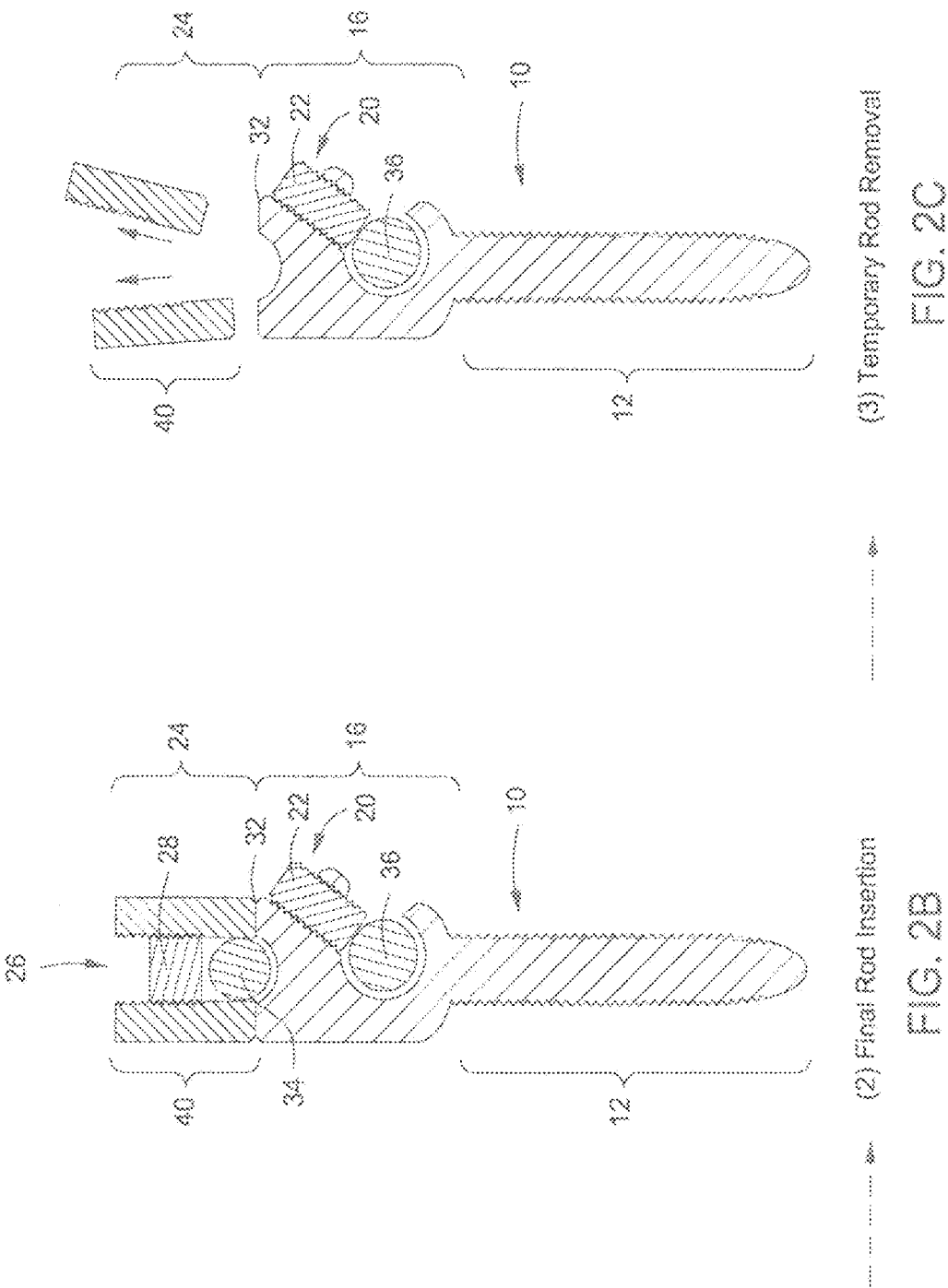

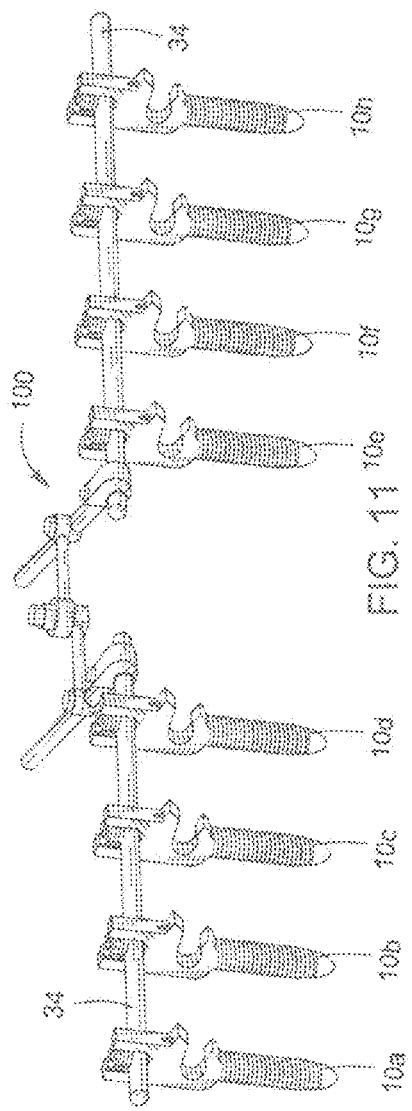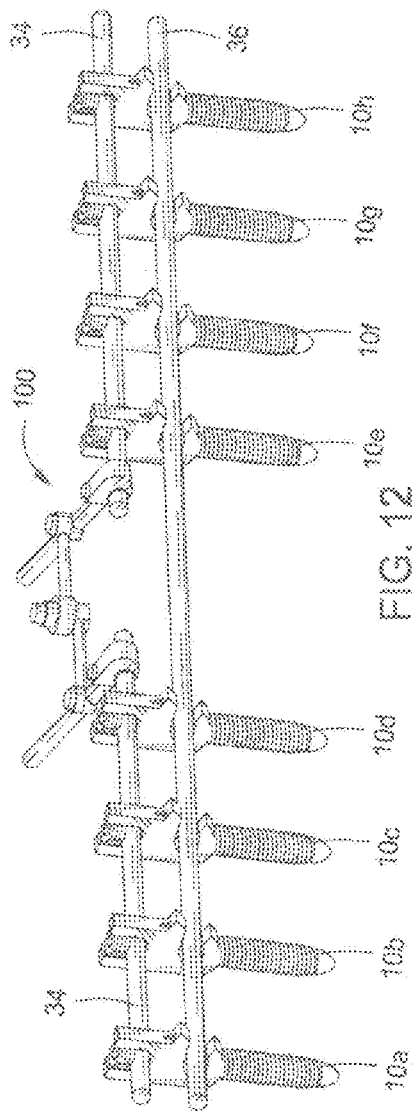

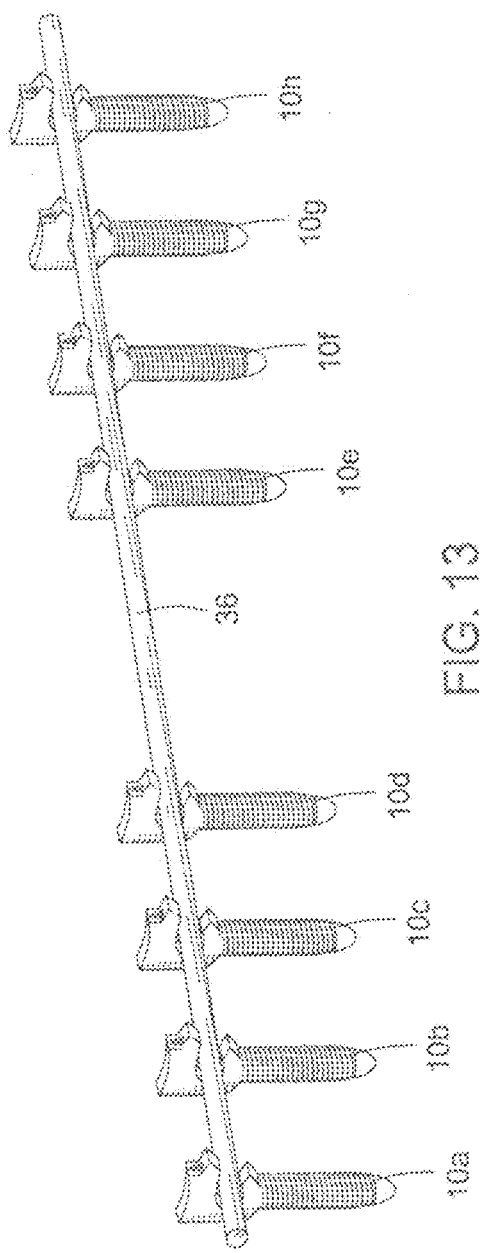

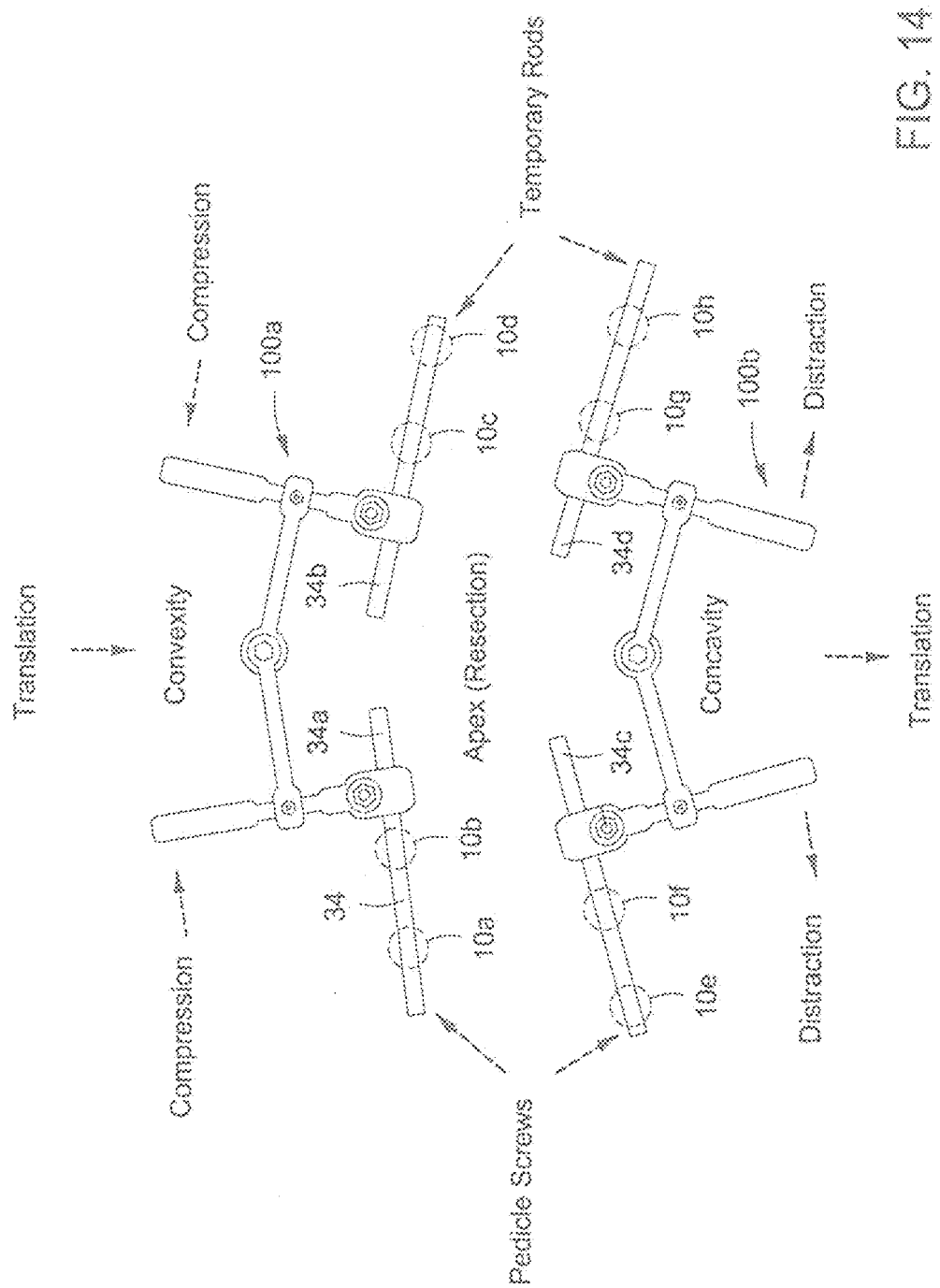

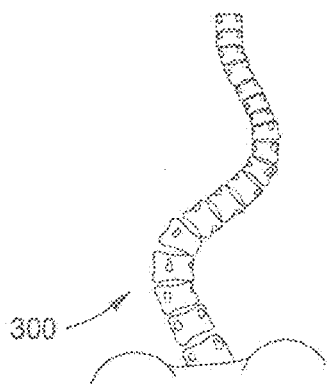
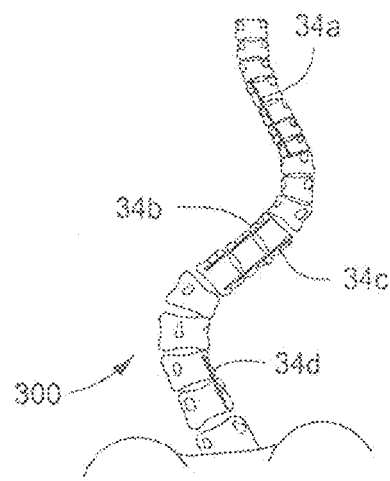
FIG. 17A
FIG. 17B
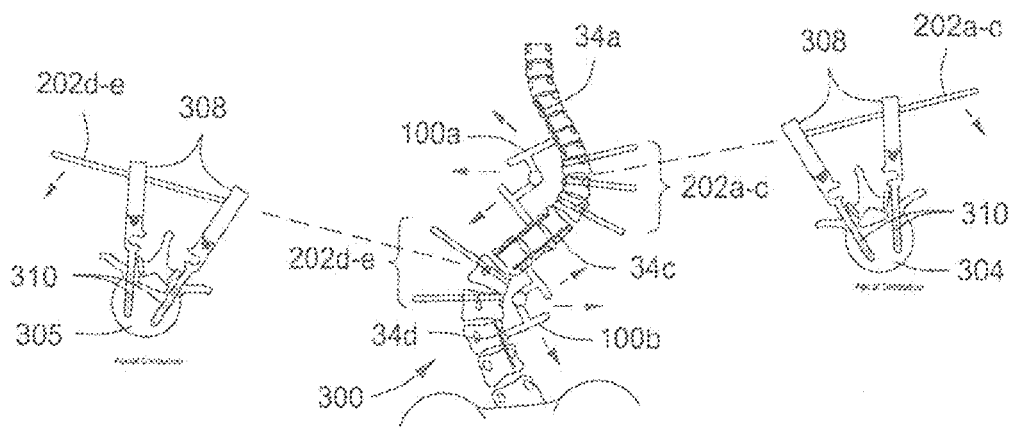
FIG. 17C
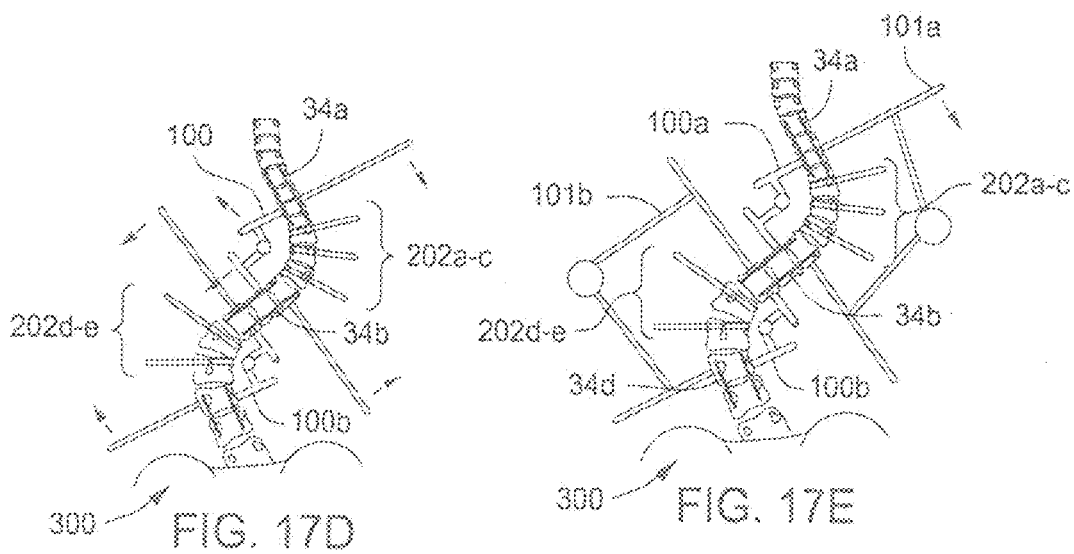
FIG. 17D
FIG. 17E

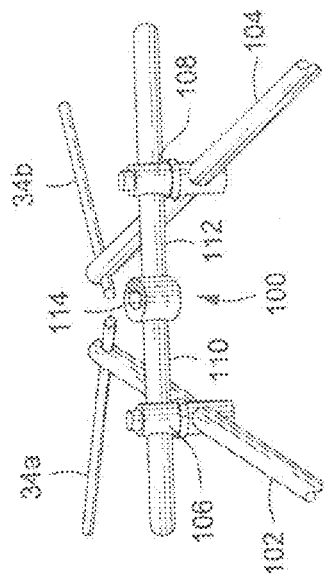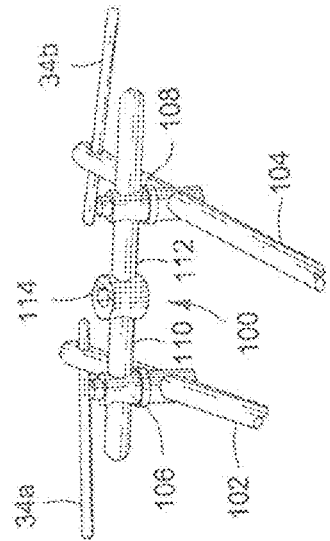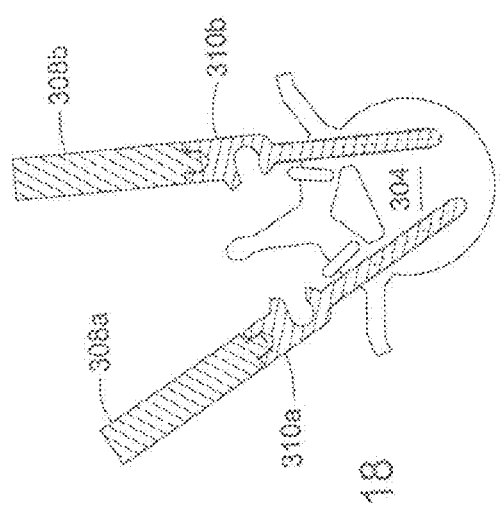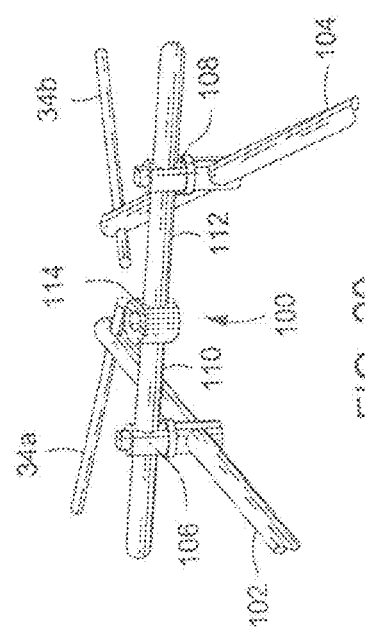

PEDICLE SCREW

CROSS-REFERENCE TO RELATED APPLICATIONS

This patent application is a divisional patent application of U.S. patent application Ser. No. 12/364,423 filed on Feb. 2, 2009 and entitled "Pedicle Screw," which is a non-provisional patent application of and claims priority to U.S. Provisional Application Ser. No. 61/025,760 filed Feb. 2, 2008 and U.S. Provisional Application Ser. No. 61/080,150 filed Jul. 11, 2008, the entire contents of each of which are incorporated herein by reference.

STATEMENT OF FEDERALLY FUNDED RESEARCH

None.

INCORPORATION-BY-REFERENCE OF MATERIALS FILED ON COMPACT DISC

None.

TECHNICAL FIELD OF THE INVENTION

The present invention relates in general to the field of bone fixation, and more particularly, to a novel pedicle screw for use in the correction of mild to severe spinal deformities.

BACKGROUND OF THE INVENTION

Without limiting the scope of the invention, its background is described in connection with pedicle screws.

In rigid severe spine deformity with coronal or sagittal decompensation, translation of the spinal column is necessary for restoration of trunk balance as well as deformity correction. However, the conventional correction methods, such as posterior correction only or anterior release and posterior instrumentation, are usually unsatisfactory. Therefore, a more aggressive approach, such as reconstructive techniques, is necessary. In 1922, Maclennan[1] first illustrated vertebrectomy and demonstrated an apical resection from a posterior-only approach with postoperative casting for the treatment of severe scoliosis. Several authors[2-8] have subsequently reported their experience with vetebrectomy, mostly for congenital scoliosis. In 1987, Bradford[9] performed both anterior and posterior vertebral column resection (VCR) with spinal shortening and posterior instrumentation and fusion demonstrating excellent restoration of coronal with relatively few complications. Leatherman[6] introduced a two-stage anterior and posterior correction procedure for congenital spinal deformity. Bradford and Bochie-Adjei[10] also reported a single stage anterior and posterior resection of hemivertebra and spinal arthordesis. However, the anterior-posterior vertebral column resection (VCR) has disadvantages such as long operative time, potential significant blood loss, and risk of intraoperative neurologic impairment due to the spinal column segment instability during the resection and the correction procedure.

In 2002, Suk[11-13] introduced a technique of a single posterior approach to perform VCR (PVCR) that offered significant advantages over the combined anterior-posterior VCR. The surgery consisted of temporary stabilization of the vertebral column with segmental pedicle screw fixation, resection of the vertebral column at the apex of the deformity via the posterior route followed by gradual deformity correction and global fusion. In the surgical technique, multiple pedicle screws were utilized proximal and distal to the vertebral resection to securely fix the spine prior to any bony resection. Provisional single rod placement is performed during the bony resection to prevent sudden spinal column translations which may result in spinal cord injury. The vertebral column resection and deformity correction were carried out either by exchanging the temporary pre-contoured rods one by one or by in situ rod bending. However, these technique have a number of disadvantages: 1) the risk of intraoperative mishaps due to the instability resulting from exchanging the temporary rods may produce spinal cord injury; 2) limitation in deformity correction secondary to a "one-time" correction maneuver utilized using the Suk technique; 3) short segment fixation using the provisional rods since multiple exchanges prevent long rod utilization; and 4) additional surgical time necessary with multiple removal and insertion of the temporary provisional rods.

One such fixation system is taught in U.S. Pat. No. 7,220,262, issued to Hynes. Briefly, the spinal fixation system and related methods include pedicle screws secured in two columns, one along each side of the spine. Cross support rods have ends connected to pedicle screw heads. A longitudinally extending rod is supported on the cross supports and recessed in the cavity created by removal of portions of spinous processes, providing a reduced profile of the installed construct. Several types of cross supports are shown such as: arms from the screws inward to rings or yokes connecting the longitudinal rod; cross rods with ends connected to the screws and having centrally-located yokes for the longitudinal rod; cross rods with articulating longitudinal rod portions fixed or swiveled to them. These cross rods may have end portions angled posterior toward anterior to accommodate lateral positioned pedicle screws, but shorter cross rods without angled end portions enable medialized pedicle screw orientation.

U.S. Pat. No. 7,163,539, issued to Abdelgany, et al., is directed to a biased angle polyaxial pedicle screw assembly. Briefly, a pedicle screw assembly and method of assembly is taught that comprises a longitudinal member; a screw head comprising a bulbous end, wherein the screw head has a slot adapted to receive the longitudinal member; a bone fixator component comprising a concave socket having a biased angled top and a rounded bottom adapted to receive the screw head; a locking pin adapted to engage the screw head, the bone fixator component, and the longitudinal member; and a blocker adapted to engage the screw head and to secure the longitudinal member. Additionally, the bone fixator component may be configured as any of a bone screw and a hook.

Yet another system is taught in U.S. Pat. No. 6,488,681, issued to Martin, et al., for a pedicle screw assembly. Briefly, a stabilizing assembly is taught that includes a fastener having an upper end and a lower end, a head at the upper end, and at least one anchoring element extending between the upper and lower ends. The head includes a center, an underside including a first radial surface and a top side including a second radial surface. The first radial surface of the head defines a first radius from the center of the head and the second radial surface defines a second radius from the center of the head, the first radius being greater than the second radius. The assembly also includes a coupling element having an upper end and a lower end, the coupling element including a rod receiving opening extending from the upper end thereof being adapted to receive a stabilizing rod, a bore extending through the lower end of the coupling element for receiving the fastener, and a conical-shaped seat adjacent the lower end of the coupling element adapted to engage the first radial surface of the head when the fastener is positioned in the bore. A locking element associated with the coupling element is adapted to apply a force upon a stabilizing rod positioned in the rod receiving opening. As a force is applied to a stabilizing rod, the rod in turn, engages the second radial surface at the top side of the head for forcing the underside of the head against the conical-shaped seat of the coupling element so as to prevent further pivotal and rotational movement of the fastener and the coupling element relative to one another. In certain embodiments, the fastener may be a screw fastener having screw threads. In other embodiments, the fastener may include a hook.

United States Patent Application No. 20070270810, filed by Sanders is directed to a pedicle screw spinal rod connector arrangement. Briefly, a pedicle screw spinal rod connector arrangement is provided that includes in a body having an opening for mounting a head of an inserted pedicle screw. A bracket connected with the body forms a lateral restraint. A bridge is connected with and extends over the body. A spinal rod-receiving slot is provided between the bridge and the bracket. The connector arrangement also has a wedge axially offset from the pedicle screw moveable downward by a setscrew mounted with the bridge. The wedge imparts a locking force on the pedicle screw head and a generally lateral locking force on the spinal rod.

Yet another example is shown in United States Patent Application No. 20070233062, filed by Berry for a pedicle screw system with offset stabilizer rod. In this example, an improved pedicle screw system is provided with an offset stabilizer rod for the internal fixation of the spine. The pedicle screw system includes at least two multi-angle pedicle screw units adapted for anchored securement to patient bone, and an elongated stabilizer rod extending therebetween. Each pedicle screw unit includes a bone screw associated with an anchor bracket defining a laterally offset and upwardly open channel or trough for receiving and supporting the stabilizer rod. A securement member such as a set screw is fastened to the anchor bracket for compressively retaining the stabilizer rod within the bracket channel or trough. The securement member may also bear against the associated bone screw for compressively retaining the screw in position relative to the anchor bracket.

SUMMARY OF THE INVENTION

The present invention solves various problems of current pedicle screw and spinal fixation systems. The present invention allows the surgeon to stabilize the spine, effectively derotate the spine, safely translate the spine and when required easily derotate and translate the spine to treat spinal deformities.

The present inventors recognized there and other disadvantages of the current implant strategies used during Posterior Vertebral Column Resection (PVCR) by designing a new pedicle screw posterior instrumentation system. The present invention includes screws, methods, kits and systems that provide a safer, easier and better correction, as well as shorter operation time method for the PVCR of the severe spinal deformity. The present invention takes advantage of the top-loading and side-loading current designs as well as a universal connecting link to provide three-dimensional correction. These components provide: 1) continued stabilization of the spine during bony resection as well as correction; 2) allow for controlled correction of the spine using both rods; and 3) provide the ability to place the permanent rods while the long provisional rod is in places so instability is not created.

The present invention includes: 1) a pedicle screw with a screw head that can receive two rods. The bone screw head includes two rod-receivers. One receiver member is basic "U" shape (top-loading component) that extends from the top of the screw head to receive a temporary rod. Another receiver member has a basic "C" shape (side-loading component) that is inferior to the first receiver. The second receiver receives a final rod. There is also a breakaway mechanism between the first and second apertures so that the first aperture can be removed while the final rod is fixed; 2) rod-link reducer has a basic "H" shape that rigidly links and locks the temporary rods, which allows attachment to the rod at any orientation in the coronal, sagittal, and transverse planes so as to make compression, distraction, derotation and cantilever method; 3) reduction handle connects with the rod-link reducer; and 4) 5.5 mm diameter rod. For the PVCR of severe spinal deformity, this instrumentation system would provide: 1) better maintenance of spinal stability throughout the surgical procedure to reduce risk of the spinal cord injuries; 2) more reliable reconstruction of the vertebral column; 3) better and easier correction of the deformity; and 4) shorter operative time.

More particularly, the present invention includes a pedicle screw that includes: a bone fastener and a rod coupling head, the rod coupling head comprising a lower and an upper rod coupling, wherein the lower rod coupling has a lateral rod opening adapted to receive a permanent rod; an angled bore extends into the lateral rod opening; and a permanent rod fastener in the angled bore to engage a permanent rod in the lateral rod opening; and the upper rod coupling has an upper rod opening adapted to receive a temporary rod, wherein the upper rod opening is formed to receive a temporary rod fastener, wherein the upper rod coupling is detachable from the lower rod coupling at a transition; wherein a temporary rod is temporarily affixed into the upper rod opening during a bone realignment and a permanent rod is positioned in the lateral rod opening and engaged by the permanent rod fastener upon final bone alignment. In one aspect, the lower and upper rod couplings are integral and the transition between the first and second coupling assemblies is breakable. In another aspect, the lower and upper rod couplings are integral and a transition between the first and second coupling assemblies is semi-permanently attached.

The transition between the lower and upper rod couplings comprises a universal joint, a pivot, a slot, a collar, a bearing, a dove-tail, a ball-joint, a gimbal, a level, or a sleeve. The pedicle screw may also include lateral and upper rod openings that are generally perpendicular or parallel. In one aspect, the temporary fastener, the permanent fastener or both fasteners threadably engage the temporary rod, the permanent rod or both rods. In another aspect, the temporary, the permanent or both fasteners are locking pins. In one embodiment, the transition between the lower rod coupling and the bone fastener comprises a universal joint, a pivot, a slot, a collar, a bearing, a dove-tail, a ball-joint, a gimbal, a level, or a sleeve.

In another embodiment, the present invention includes a method of spinal fixation using pedicle screws by fastening two or more pedicle screw into two or more vertebra, the pedicle screw including a bone fastener and a rod coupling head, the rod coupling head comprising separate lower and upper lower rod couplings: the lower rod coupling including a lateral rod opening adapted to receive a permanent rod; an angled bore extends into the lateral rod opening; and a permanent rod fastener in the angled bore to engage a permanent rod in the lateral rod opening; and the upper rod coupling including an upper rod opening adapted to receive a temporary rod, wherein the upper rod opening is formed to receive a temporary rod fastener, wherein the upper rod coupling is detachable from the lower rod coupling at a transition; interconnecting the pedicle screws with a temporary rod. Next, the method includes correcting the position of the spine by manipulating the temporary rod attached to the pedicle screws; interconnecting the pedicle screws with a permanent fixation rod; and removing the temporary rod and the upper rod coupling from the two or more pedicle screws.

In one aspect of the method of the present invention, the lower and upper rod couplings are integral and the transition between the first and second coupling assemblies is breakable. In another aspect, the lower and upper rod couplings are integral and a transition between the first and second coupling assemblies is semi-permanently attached. The transition between the lower and upper rod couplings comprises a universal joint, a pivot, a slot, a collar, a bearing, a dove-tail, a ball-joint, a gimbal, a level, or a sleeve. The method of the present invention also includes using a rod link reducer to perform the step of correcting the spine.

In another embodiment, the present invention includes a kit that includes two or more pedicle screw into two or more vertebra, the pedicle screw comprising a bone fastener and a rod coupling head, the rod coupling head having separate lower and upper lower rod couplings: the lower rod coupling including a lateral rod opening adapted to receive a permanent rod; an angled bore extends into the lateral rod opening; and a permanent rod fastener in the angled bore to engage a permanent rod in the lateral rod opening; and a upper rod coupling including: an upper rod opening adapted to receive a temporary rod, wherein the upper rod opening is formed to receive a temporary rod fastener; and two or more temporary rod fasteners. The kit may also include at least one of: a permanent rod and a temporary rod; one or more rod link reducers; and one or more leverage handles.

BRIEF DESCRIPTION OF THE DRAWINGS

For a more complete understanding of the features and advantages of the present invention, reference is now made to the detailed description of the invention along with the accompanying figures and in which:

FIGS. 2A to 2C show a cross-sectional view of the pedicle screw 10 in operation.

FIGS. 11 to 13 show the first step in a spinal fixation process.

FIG. 14 shows the use of the rod link reducer and pedicle screw of the present invention.

FIGS. 17A to 17E shows the invention in use a procedure for correction of a double major severe spinal curve (Thoracic and Lumbar curve).

FIG. 18 is a detailed view of one embodiment of an apical derotation without linking the two pedicle screws.

FIG. 19 is an isometric view of a design of the rod-link reducer of the present invention.

FIG. 20 is an isometric view rod-link reducer of the present invention.

FIG. 21 is an isometric view of another design of the rod-link reducer of the present invention.

DETAILED DESCRIPTION OF THE INVENTION

Figure 1:
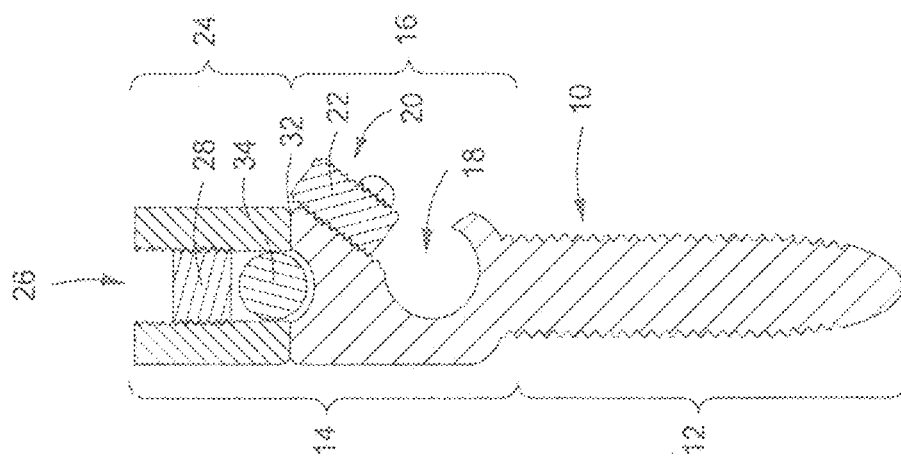
FIG. 1 shows one embodiment of the pedicle screw 10 of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The treatment of severe rigid spinal deformity is a demanding and difficult surgical challenge. The PVCR has been considered to be an effective alternative to the conventional anteriorposterior VCR in severe rigid spinal deformity. However, the current implant strategies used during PVCR afford the limited correction, potential risk of spinal cord injuries, and long operative time. This new instrumentation system may offer: 1) better maintenance of spinal stability throughout the surgical procedure to reduce risk of the spinal cord injuries; 2) more reliable reconstruction of the vertebral column; 3) better and easier correction of the deformity; and 4) shorter operative time.

Implant Components: The instrumentation system may include one or more of the following components: a pedicle screw, a rod-link reducer, reduction handle, temporary long rod, and final rod. The pedicle screw includes a threaded shank for insertion into the bone and a screw head having a first aperture and a second aperture. The first aperture has a basic "U" (tulip) shape (top-loading component) that extends from the top of the screw head and is open on both sides of the screw head to receive a first longitudinal member (a temporary rod) and a set of female threads formed in the inner walls of the first aperture. A first compression member engages the set of female threads of the first aperture and the face of the first compression member contacts the first longitudinal member. The second aperture has a basic "C" shape (side-loading component) that lines up superior to the threaded shank and inferior to the first aperture. The second aperture is open on both sides of the head to receive a second longitudinal member (a final rod). The second aperture also includes a second set of female threads that accommodate a second compression member that screwably engages the second set of female threads and the face of the second compression member contacts the second longitudinal member. There is a breakaway mechanism between the first and second apertures.

The rod-link reducer has a basic "H" shape that rigidly links and locks the first longitudinal members (temporary rods). The rod-link reducer includes: 1) two top-tightening locking mechanisms (break-off set screws) those provide access ensure the adequate grip on the temporary rods by the set screws; 2) an adjustable central mechanism by functioning in a multi-axial manner, allows attachment to the rod at any orientation in the coronal, sagittal, and transverse planes. The mechanism allows to make compression, distraction, derotation and cantilever method; 3) two adjustable lateral mechanisms (break-off set screws) allow the locking mechanisms adequately to attach the temporary rods; 4) two squared ends those connect with two reduction handles.

The reduction handle is a column shape and has two portion ends. The first end has a squared access that connects with the squared end of the rod-link reducer. The second end is a solid column. The temporary rod and the final rod are the diameter of 5.5 mm rods those are made of stainless steel or titanium.

In operation, the present invention may be used as follows: With the spine exposed posteriorly, the pedicle screws will be inserted segmentally, except for the resected levels (apex). The spine is then divided into cephalad and caudal portions by the resected levels. At the cephalad portion, two temporary rods will be fixed on the convex and concave side via the first aperture of the pedicle screw respectively. Another two temporary rods will be similarly fixed at the caudal portion. The two temporary rods on the concave side will be connected with a rod-link reducer and locked to the shape of the deformity without any attempt at correction. Resection of the vertebral column will be performed at the convex side of the apex. Following resection on the convex side, another rod-link reducer will be connected and locked on the two convex temporary rods. The resection of the remaining vertebra will be performed on the concave side.

Deformity correction is performed by loosening the adjustable central mechanism of the rod-link reducer on the convex side with the reduction handles, which will be gradually compressed to shorten the resected gap. During the compression the resected gap on the convexity, the central part of rod-link reducer on the concavity will be gradually loosen to match the compression/shortening on the convexity.

After deformity correction, two final rods will be fixed on the convex and concave side via the second aperture of the pedicle screw respectively. The two rod-link reducers will be unlocked and all temporary rods will be removal. A custom wrench will be used to remove the first aperture parts of the pedicle screw.

The pedicle screw and any of its components including the bone fastener, threads, neck and screwhead, may be made of a non-organic material that is durable and that can be implanted in a human body, such as titanium, stainless steel, spring steel, aluminum, Niobium, carbon fiber, ceramics, polymers, composites or any relatively hard material (e.g. Titanium-Aluminum-Niobium-alloy). Generally, the material selected will be biocompatible, that is, compatible with the surrounding bone and tissue.

The present invention provides a substantial improvement in addressing clinical problems indicated for surgical treatment of chronic or acute spinal injuries, including traumatic spinal injuries, scoliosis (abnormal lateral curvature of the spine), kyphosis (abnormal forward curvature of the spine, often in the thoracic spine), excess lordosis (abnormal backward curvature of the spine, often in the lumbar spine), spondylolisthesis (forward displacement of one vertebra over another, often in a lumbar or cervical spine) and other disorders caused by abnormalities, disease or trauma, such as ruptured or slipped discs, degenerative disc disease, fractured vertebra, and the like.

FIG. 1 shows one embodiment of the pedicle screw 10 of the present invention. The pedicle screw 10 includes a bone fastener 12 and a rod coupling head 14. The rod coupling head 14 includes a lower rod coupling 16 having a lower rod opening 18, depicted in a lateral configuration. The lower rod opening 18 may have any angle so long as the material of the pedicle screw 10 that surrounds the lower rod opening 18 is sufficiently strong to retain and affix a permanent rod. The lower rod coupling 16 also includes a bore 20, through which a permanent rod fastener 22 can be inserted to fasten a permanent rod. As in the case of the lower rod opening 18, the material of the pedicle screw 10 surrounding the bore 20 will also be sufficiently strong to retain and affix a permanent rod. The upper rod coupling 24 has an upper rod opening 26. The upper rod coupling 24 is formed to permit the user to insert a temporary rod using a temporary rod fastener 28. The lower and upper rod couplings 16 and 24, respectively, will often be made of unitary construction. For illustration purposes, and not necessarily as an element or limitation, a transition 32 is denoted. In unitary embodiments, the transition 32 may be modified (e.g., notched, cut, scratched or weakened) to provide for the breakage of the upper rod coupling 24. In another embodiment, the transition 32 may provide a semi-permanent attachment between the lower rod coupling 16 and the upper rod coupling 24, such that the transition is a universal joint, a pivot, a slot, a collar, a bearing, a dove-tail, a ball-joint, a gimbal, a level, or a sleeve. Likewise, the lower rod coupling 16 and the bone fastener 12 may be connected with a universal joint, a pivot, a slot, a collar, a bearing, a dove-tail, a ball-joint, a gimbal, a level, or a sleeve. When made in a unitary construction, the pedicle screw 10 may be machined, sintered, cast, welded or glued as long as the pedicle screw 10 is of sufficient strength for the bone fixation application.

Figure 2A:
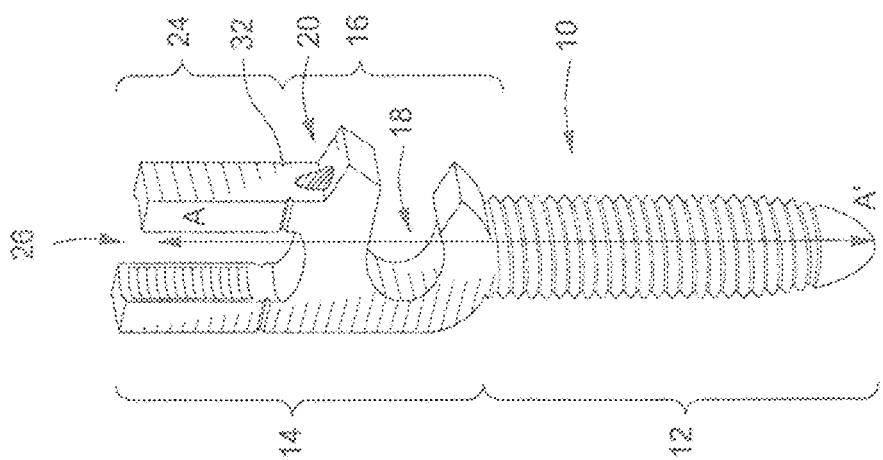

FIGS. 2A to 2C show a cross-sectional view of the pedicle screw 10 in operation. In FIG. 2A, the pedicle screw has been affixed to a bone (not depicted) and a temporary rod 34 has been inserted into the upper rod opening 26 and semi-permanently affixed using the temporary rod fastener 28. In the embodiment depicted, the upper rod opening 26 is shows internally threaded and the temporary rod fastener 28 is shows externally threaded. The skilled artisan will recognize that the present invention also includes fastener embodiments in which the threading is reversed, the threading is external to the upper rod coupling and the fastener is internally threaded, the fastener is a cap, the fastener and the coupling snap together, are wedged together, twist and lock. Likewise, the permanent rod fastener is also able to engage the permanent rod in a variety of manners, including pins, latches, threading, snapping, wedging and locking. The permanent rod may even be glued or welded.

FIG. 2B shows the addition of the permanent rod 36 in addition to the temporary rod 34. Next, the temporary rod fastener 28 and the temporary rod are removed (not depicted). Finally, FIG. 2C shows the final assembly in which the upper rod coupling is removed completely by breaking the upper rod coupling into tabs 40 at breakpoints 38.

Figure 3A:
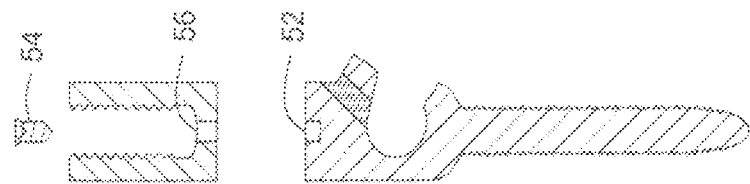
FIGS. 3A and 3B show an isometric view and a cross-sectional view, respectively, of the pedicle screw 10.
Figure 3B:
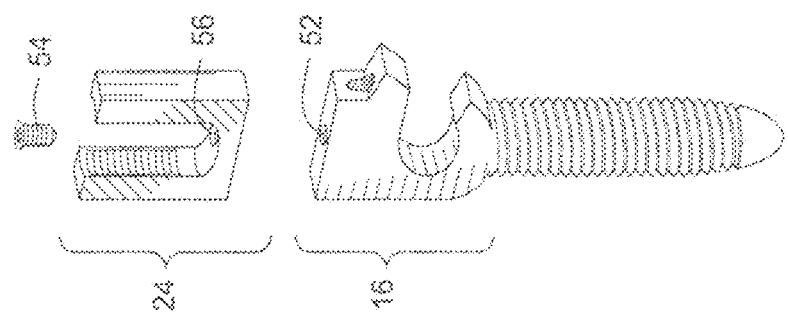

FIGS. 3A and 3B shows an isometric view and a cross-sectional view, respectively, of the pedicle screw 10 in which the lower rod coupling 16 and the upper rod coupling 24 are connected by in which a screw portion 50 is fastened into opening 52 and which permits the potential for some rotations about the axis of the screw portion 50. After the permanent rod has been affixed into the pedicle screw 10, the upper rod fastener 24 is removed.

FIGS. 3A and 3B show an isometric view and a cross-sectional view, respectively, of the pedicle screw 10 in which the lower rod coupling 16 and the upper rod coupling 24 are connected by in which a screw portion 50 is fastened into opening 52 and which permits the potential for some rotations about the axis of the screw portion 50. After the permanent rod has been affixed into the pedicle screw 10, the upper rod fastener 24 is removed.

Figure 4A:
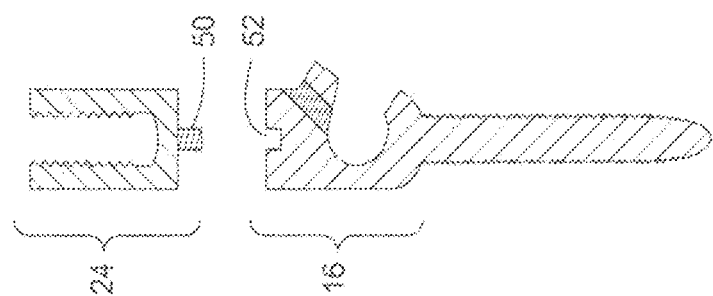
FIGS. 4A and 4B show an isometric view and a cross-sectional view, respectively, of the pedicle screw 10.
Figure 4B:
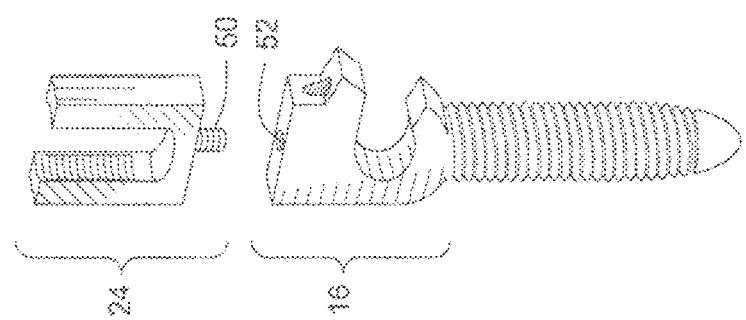

FIGS. 4A and 4B show an isometric view and a cross-sectional view, respectively, of the pedicle screw 10 in which the lower rod coupling 16 and the upper rod coupling 24 are connected by in which a screw 54 is fastened through opening 56 into opening 52 and which permits the potential for some rotations about the axis of the screw 54. After the permanent rod has been affixed into the pedicle screw 10, the upper rod fastener 24 is removed by unscrewing screw 54. The screw 54 also permits control over the mechanical force required to rotate the upper rod coupling 24. For configurations in which the lower rod coupling 16 and the upper rod coupling 24 are separate, the interface between the two make be smooth, rough or patterned (e.g., random or non-random) or coated.

Figure 5B:
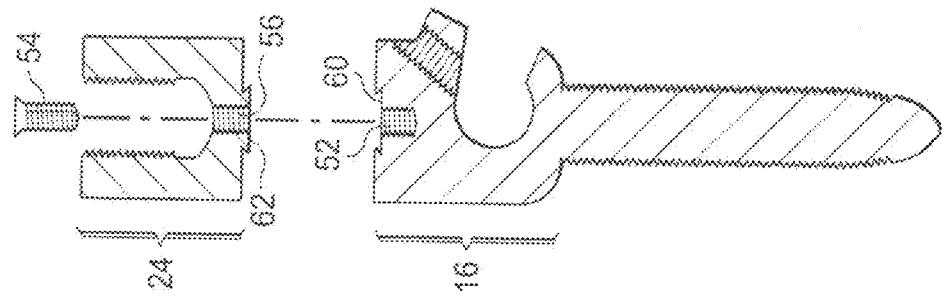
FIGS. 5A and 5B show an isometric view and a cross-sectional view, respectively, of the pedicle screw 10.
Figure 5A:
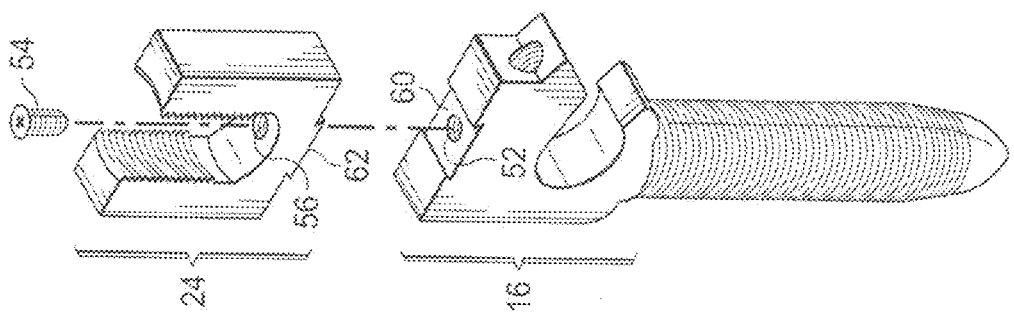

FIGS. 5A and 5B show an isometric view and a cross-sectional view, respectively, of the pedicle screw 10 in which the lower rod coupling 16 and the upper rod coupling 24 are connected by in which a screw 54 is fastened through opening 56 into opening 52 and which permits the potential for some rotations about the axis of the screw 54. After the permanent rod has been affixed into the pedicle screw 10, the upper rod fastener 24 is removed by unscrewing screw 54. In this configuration the lower rod coupling 16 and the upper rod coupling 24 are separate and the interface between the upper and lower rod couplings (24, 16) is enhanced by the addition of a slit 60 that dove-tails with a notch 62. The notch 62 can even be placed at an angle or can also be made square such that the upper rod coupling 24 can be placed parallel or perpendicular to the direction of the permanent or temporary rods.

Figure 6B:
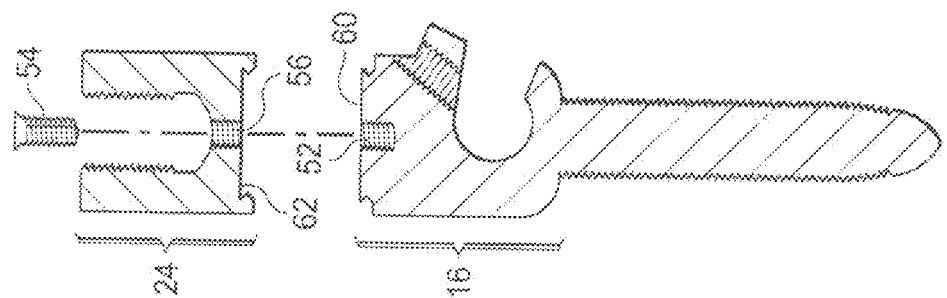
FIGS. 6A and 6B show an isometric view and a cross-sectional view, respectively, of the pedicle screw 10.
Figure 6A:
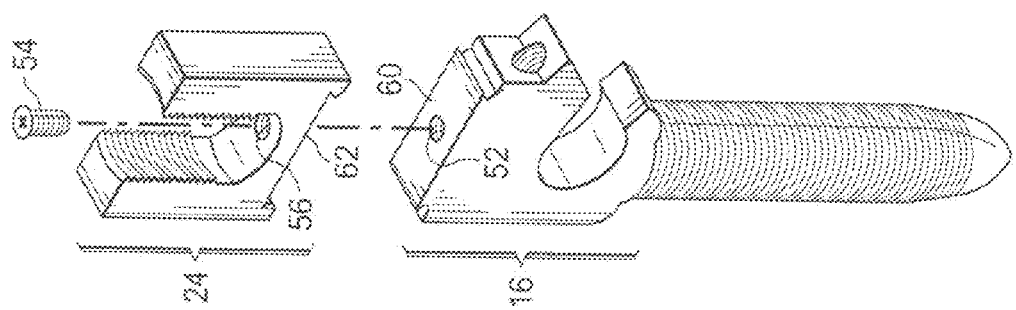

FIGS. 6A and 6B show an isometric view and a cross-sectional view, respectively, of the pedicle screw 10 in which the lower rod coupling 16 and the upper rod coupling 24 are connected by in which a screw 54 is fastened through opening 56 into opening 52 and which permits the potential for some rotations about the axis of the screw 54. After the permanent rod has been affixed into the pedicle screw 10, the upper rod fastener 24 is removed by unscrewing screw 54. In this configuration the lower rod coupling 16 and the upper rod coupling 24 are separate and the interface between the upper and lower rod couplings (24, 16) is enhanced by the addition of a slit 60 that dove-tails with an external notch 62. The notch 62 can even be placed at an angle or can also be made square such that the upper rod coupling 24 can be placed parallel or perpendicular to the direction of the permanent or temporary rods.

Figure 7B:
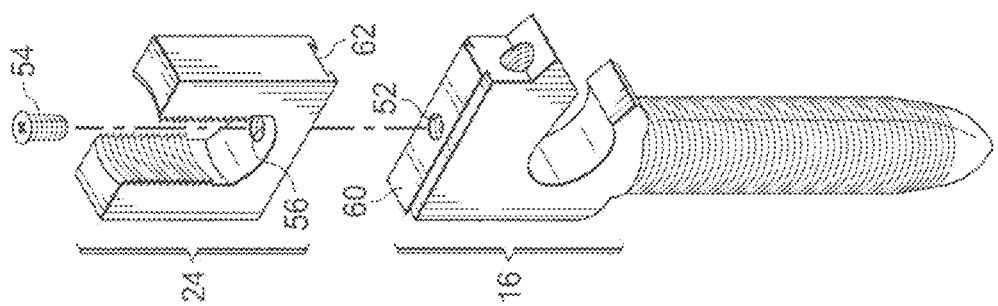
FIGS. 7A and 7B show an isometric view and a cross-sectional view, respectively, of the pedicle screw 10.
Figure 7A:
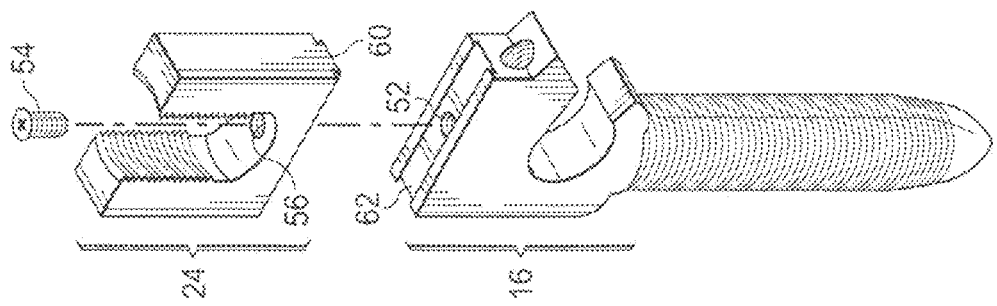

FIGS. 7A and 7B show an isometric view and a cross-sectional view, respectively, of the pedicle screw 10 in which the lower rod coupling 16 and the upper rod coupling 24 are connected by in which a screw 54 is fastened through opening 56 into opening 52 and which permits the potential for some rotations about the axis of the screw 54. After the permanent rod has been affixed into the pedicle screw 10, the upper rod fastener 24 is removed by unscrewing screw 54. In this configuration the lower rod coupling 16 and the upper rod coupling 24 are separate and the interface between the upper and lower rod couplings (24, 16) is enhanced by the addition of dove-tail joints (shown in two different configurations). The notch 62 can even be placed at an angle or can also be made square such that the upper rod coupling 24 can be placed parallel or perpendicular to the direction of the permanent or temporary rods.

Figure 8:
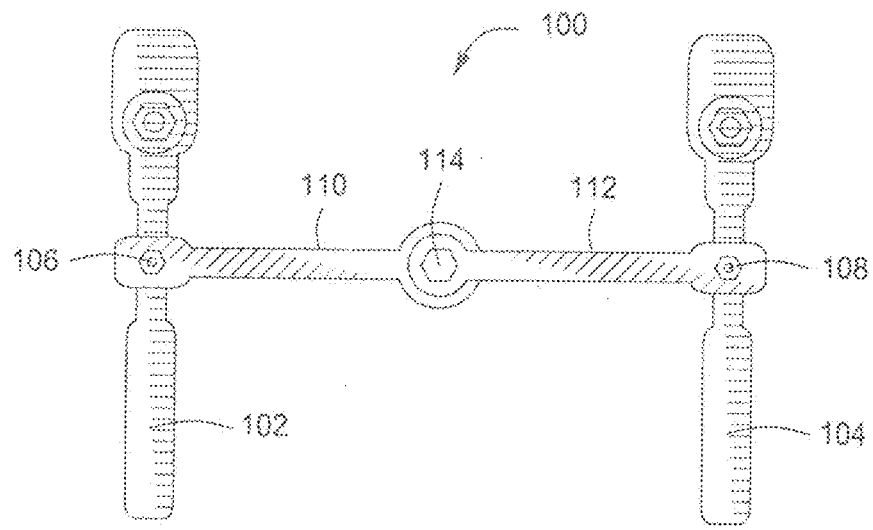
FIG. 8 shows a rod link reducer 10 for use with the present invention.

FIG. 8 is an isometric view of a rod link reducer 100 for use with the present invention. The rod link reducer 100 includes first and second spinal rod manipulators 102, 104, which are connected to a first spinal rod manipulator joint 106 connected to the first spinal rod manipulator 102 and a second spinal rod manipulator joint 108 connected to the second spinal rod manipulator 104. First and second translatable transverse shafts 110, 112 connected to the first and second joints 106, 108, respectively, which connected to a reducer 114 connected to both the first and second translatable transverse shafts 110, 112, wherein the reducer 114, the shafts 110, 112 and the linkers 106, 108 provide movement and temporary fixation of a spine that has been manipulated into a final position during spinal surgery.

Figure 9:
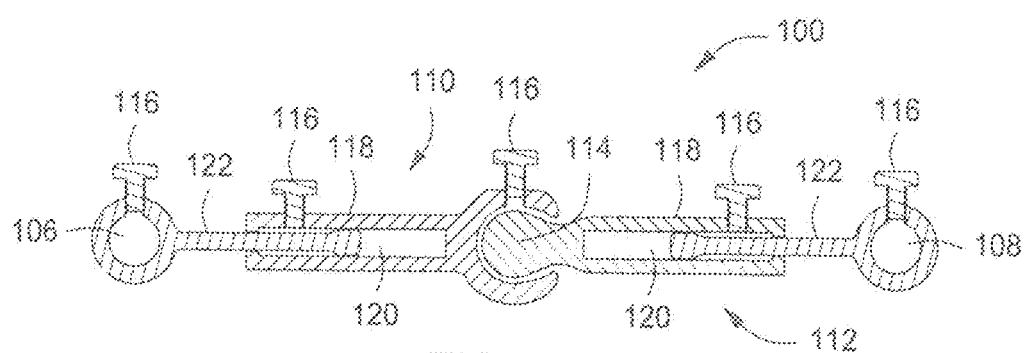
FIG. 9 is a cross-sectional side view of one embodiment of the rod link reducer 10 present invention.

FIG. 9 is a cross-sectional side view of one embodiment of the rod link reducer 10 present invention, shown in this embodiment with screws 116. The skilled artisan will recognize that the screws 16 provide reversible mechanical fixation between the different parts of the system that can be tightened and loosened during spinal adjustments. Any given joint may include some friction or resistance during use up to and including total fixation. The screws 116 can be replaced or include pins, set screws, cotter pins, internal or external compression, compression fittings, collared fittings, screw-drives or even electrical, pneumatic or hydraulic movement or pressure. In the embodiment depicted, first and second translatable transverse shafts 110, 112 as shown as adjustment sleeves slidably fitted within a housing 118 is an axial bore 120 and within the axial bore a strut 122 in which the screw 116 serves as a fastener positioned to secure the strut 122 within the housing 118, wherein the struts 112 allow for coarse longitudinal movement of the strut 122 with respect to the strut housing 118. The skilled artisan will recognize that the strut-bore configuration can be reversed (bore-strut) or replaced with side-by-side struts, internal-external slidable pins within a groove, screw-drives, magnetic drives, electrical, pneumatic or hydraulic drives so long as the translatable transverse shafts 110, 112 permit the user to expand and/or contract one or both the translatable transverse shafts 110, 112.

Figure 10:
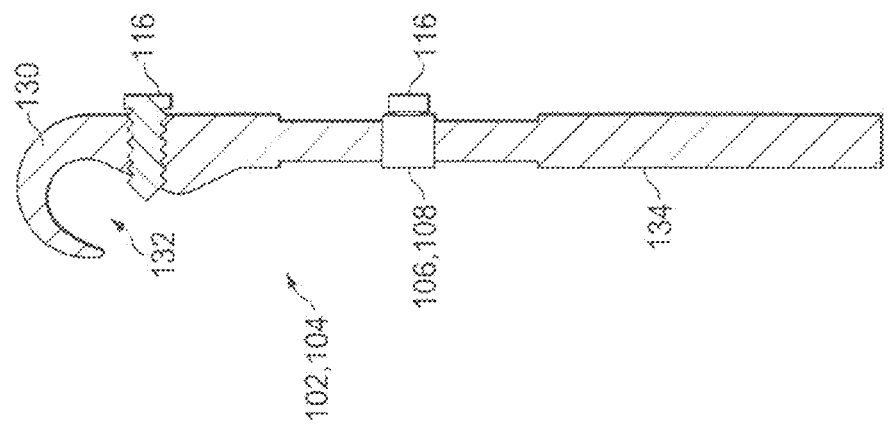
FIG. 10 is a side view of one embodiment of a rod manipulator.

FIG. 10 is a side view of one embodiment of rod manipulators 102, 104. In this side view screws 116 are shown as well as either first or second joint 106, 108. The rod manipulators 102, 104 include a head 130 that has an opening 132 that first a rod (temporary or permanent) for spinal fixation. The screw 116 is used to engage and retain the rod. The rod manipulators 102, 104 will be made from a material with sufficient tensile strength to allow the manipulator to fasten to the rod but also to permit the user to translate movement from the handle 134 into the rod in any direction. The handle 134 may itself also include a coating (not depicted) to improve the grip of a user during use or may be shaped to permit a second handle to attach to the handle 134 to increase the leverage of a user when manipulating a spine during spinal fixation surgery. Again, while this embodiment is shown with screws, any fastening method (pins, set-screws, compression, collets, etc.) may be used to fasten the various components of the rod link reducer of the present invention.

The rod link reducer 100 may be used in conjunction with existing spinal screw and rod fixation systems or may be used in conjunction with the pedicle screw 10. The size and thickness of rods may be varied depending on the type of surgery, tensile strength required and preference of the user.

FIG. 11 shows the first step in a spinal fixation process. In this embodiment, a temporary rod 34 has been attached to pedicle screws 10 (while not depicted, the pedicle screws may be attached individual vertebra. Examples of conditions that may be treated using the present invention include kyphosis, lordosis, scoliosis or combinations thereof. A rod link reducer 100 is shown connected to the temporary rod 34 and the spine (not shown) has been aligned. In FIG. 12, the permanent rod 36 is introduced into the pedicle screw 10 while the rod link reducer 110 holds the entire assembly in place while the permanent rod is permanently affixed to the pedicle screws 10. Finally, FIG. 13 shows the final spinal rod assembly after removing the permanent rod and the breakable tabs from the pedicle screws 10.

FIG. 14 shows the advantage provided by the rod link reducer 100 of the present invention. In this top view of the operation of the present invention, two rod link reducers 100a, 100b are connected to two pairs of temporary rods 34a-d and pedicle screws 10a-h. By compressing, distracting or rotating the rod link reducers 100a, 100b, the user can manipulate the spine in all directions necessary for spinal alignment and fixation. Furthermore, the user is able to compress, distract, and translate any of the spinal segments until arriving at a final position. The rod link reducer 100 is tightened upon final positioning and the permanent rod can be inserted into the pedicle screws. Furthermore, the rod link reducers 100a, 100b can be tightened in a single plane at a time while still manipulating the rest of the spine in the other planes.

The present invention can be used to correct mild to severe spinal deformities, including sever deformities. The present invention includes the following advantages: a reduced risk of intraoperative mishaps due to the instability caused by exchanging the temporary rods with the permanent rod, it increases the directions in which the deformities can be corrected and reduces the number of tools, and surgical time caused by temporary rod failure or slipping that occurs between the final positioning of the temporary rods and the fixation of the permanent rod. It has been found that the present invention allows the surgeon to shorten the duration of the operation and also increases the extent of correction in a single procedure.

Figure 15:
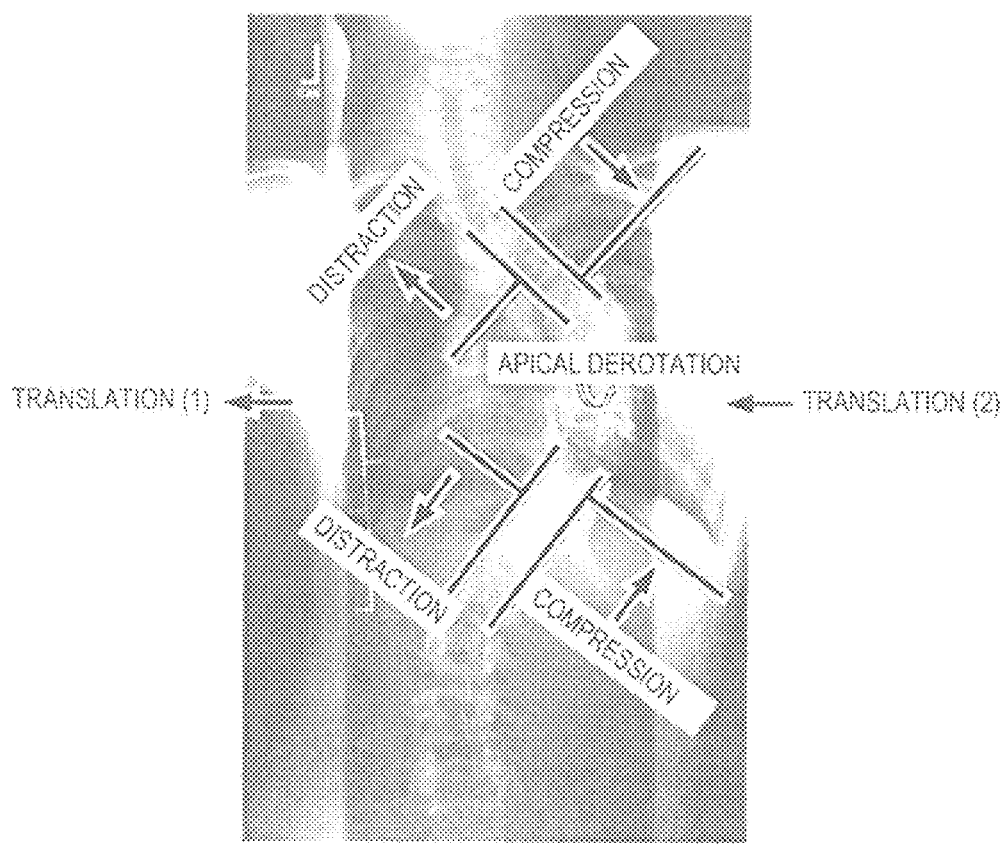
FIG. 15 shows an overlay of the planning and tools for a surgical procedure to correct a severe spinal deformity.

FIG. 15 shows an overlay of the planning and tools for a surgical procedure to correct a severe spinal deformity. An x-ray is shown of a malformed spine and the tools are overlaid to plan the positioning of the pedicle screws, rods and rod link reducer. Next, the user determines the various different steps in the correction, including the compression, distraction, apical derotation and translation of one or both pairs of temporary rods. Also shown are optional tools or handles to increase the leverage of the surgeon, taking into account the accessibility of tools due to the translation and rotation of the underlying spine prior to treatment. In certain cases, the steps may be alternated to maximize the leverage of the rod link reducers in different direction, thereby maximizing efficiency of the movement, increasing the effectiveness of the procedure and minimizing the time of the procedure.

Figure 16A:
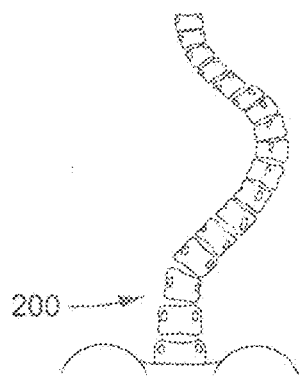
FIGS. 16A to 16E shows the invention in use a procedure that includes distraction, translation and apical derotation for correction of a single severe spinal curve.
Figure 16C:
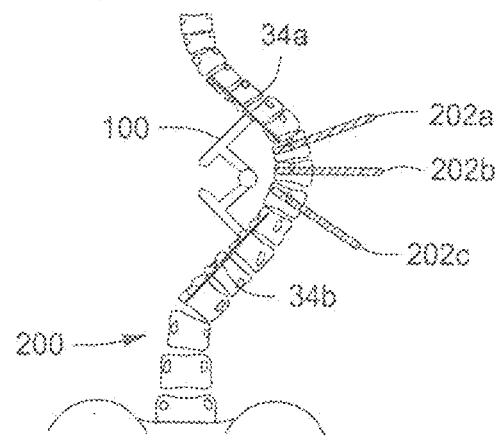
Figure 16B:
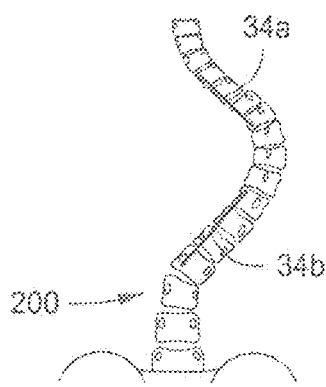
Figure 16D:
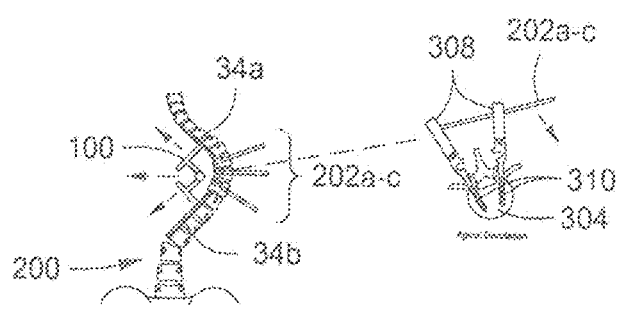
Figure 16E:
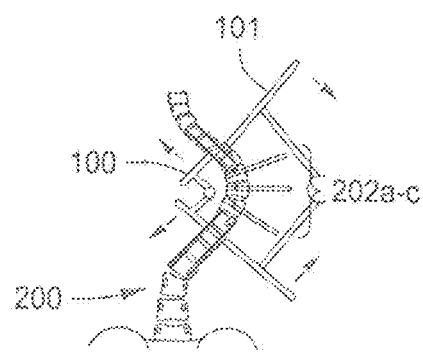
Figure 22:
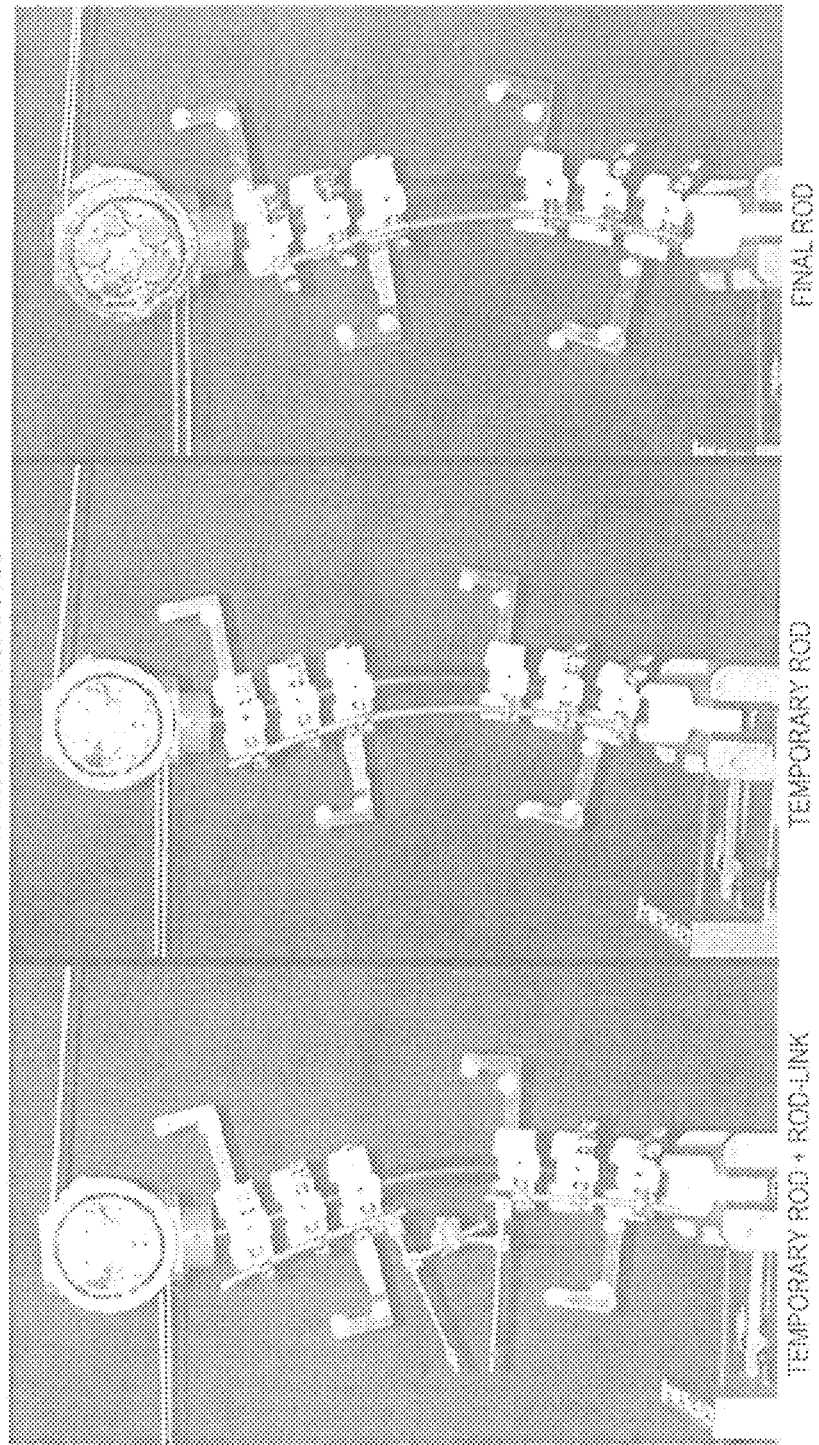
FIG. 22 shows a six-segment plastic spine model was instrumented to test three constructs: (1) temporary rod/apical rod-link reducer (left panel); (2) provisional rod (center panel); and (3) final rod (right panel).
Figure 27:
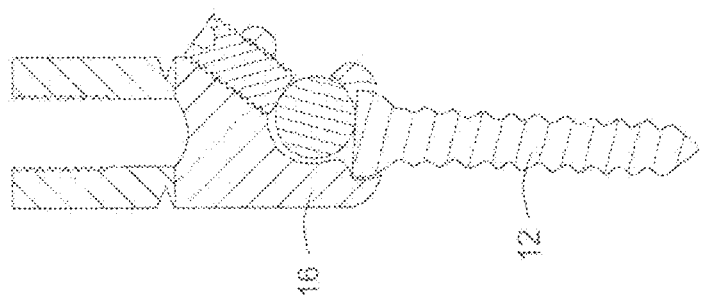
FIGS. 24-27 are illustrations showing that the bone fastener is semi-permanently attached and can receive the rod at any direction.
Figure 26:
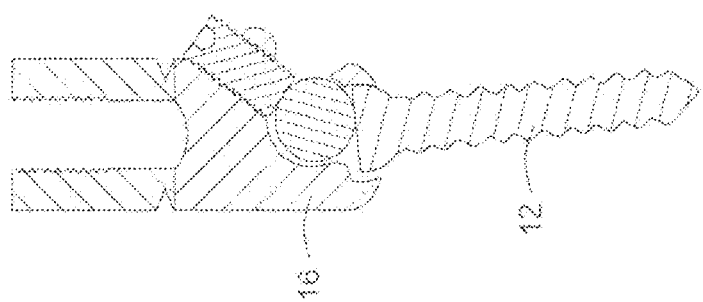
Figure 25:
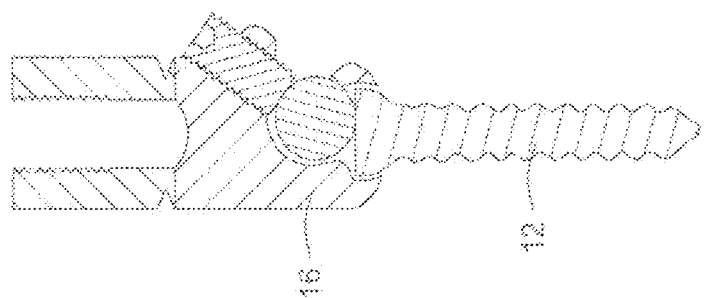

FIGS. 16A to 16E shows the invention in use a procedure that includes distraction, translation and apical derotation. FIG. 16A shows a single right thoracic rigid curve 200. FIG. 16B shows the first step in the procedure in which temporary rods 34a and 34b, which are fixed at a proximal portion of the spine and another one fixed at distal portion of the curve about a concavity. The temporary rods 34a, 34b are attached to the single right thoracic rigid curve 200 using pedicle screws (not depicted) on either end of the site for distraction, translation and apical derotation. One example of the pedicle screws that may be used in the procedure is pedicle screw 10. FIG. 16C shows the rod link reducer 100 connected to temporary rods 34a and 34b on the concavity. Next, derotation instruments 202a-c are attached to the apical vertebrae. FIG. 16D shows the combined distraction, translation and apical derotation of the spine in which the rod link reducer 100 is used for the distraction and translation (arrows) and the derotation instruments 202a-c, seen as a cross-sectional view of the spine at a vertebrae 304, is are used alone or in combination (in this instance) for apical derotation via linker 308 attached to pedicle screws 310. The skilled artisan will recognize that these tools may be used for a distraction, translation and/or apical rotation, however, most procedures will involve a combinations of these manipulations. FIG. 16E shows a variation of the combined distraction, translation and apical derotation outlined in FIGS. 16A-16D in which pairs of temporary rods 34a, 34b are shown in parallel along the proximal and distal segments of the spine. A second rod link reducer 101 is shown as two provisional rods 34 are on the concavity. Convex provisional compression is to help the curve correction.

FIGS. 17A to 17E shows the use of the rod link reducer 100 on a spinal convexity. FIG. 17A shows a right thoracic rigid curve 300 onto which two temporary rods 34a, 34b are on the concavity of the thoracic curve and two temporary rods 34c, 34d are on the concavity of the lumbar curve as shown in FIG. 17B. FIG. 17C shows the attachment of two rod-link reducers 100a, 100b fixed on the concavity for both curves, respectively. Next, the combined distraction, translation and apical derotation for both curves is depicted in which derotation instruments 202a-c and 202d-e are attached to the vertebrae 204, 305 through pedicle screws 306 via linkers 308. The linkers 308 serve as attachment points for the derotation instruments 202a-e and can be used to increase the leverage for the distraction, translation and apical derotation. FIG. 17E shows the positioning of a pair of convex temporary rods at each site are used for compression maneuvers to help in the correction of the two curves using two rod link reducers 100, 101 about each of the treatment sites.

FIG. 18 is a detailed view of one embodiment of an apical derotation without linking the two pedicle screws 310a, b. In this embodiment, the linkers 308a, b are used directly to aid in the apical rotation of a single vertebrae 304 without a linked derotation instrument.

FIGS. 19, 20 and 21 shows various designs of the rod-link reducer 100. FIG. 19 shows a rod link reducer 100 that includes a universal connector on the central portion. The rod link reducer 100 includes first and second spinal rod manipulators 102, 104, which are connected to a first spinal rod manipulator joint 106 connected to the first spinal rod manipulator 102 and a second spinal rod manipulator joint 108 connected to the second spinal rod manipulator 104. First and second translatable transverse shafts 110, 112 slides through joints 106, 108, respectively. The joints 106, 108 can tighten to fix the transverse shafts 110, 112 individually. In FIG. 19, the two translatable transverse shafts 110, 112 have movement around a reducer 114, which is depicted as a single reducer with universal movement. In one example, the reducer 114 may be fixed to act as a straight rod to limit the movement of the first and second spinal rod manipulators 102, 104 in two planes. FIGS. 20 and 21 show the rotation between the rod-connector. This design would be stronger and easily to install and give surgeons more free for surgery.

As the skilled artisan will appreciate the first and second translatable transverse shafts 110, 112 may be in-line, as depicted in FIGS. 19-21, or may be parallel on two separate planes allowing the first and second translatable transverse shafts to extend past the ends of the opposite shaft. By allowing the first and second translatable transverse shafts to move in parallel, the distance between first and second spinal rod manipulators 102, 104 can be reduced to a minimum in certain manipulations. As can also be seen from these figures, the first and second rod manipulator joints 106, 108 can slide toward or away from the temporary rods 34a,b. The configuration presented herein allows six degrees of freedom in any direction, while also providing the necessary strength and leverage to perform complex spinal deformity surgery in a reduced space.

Figure 24:
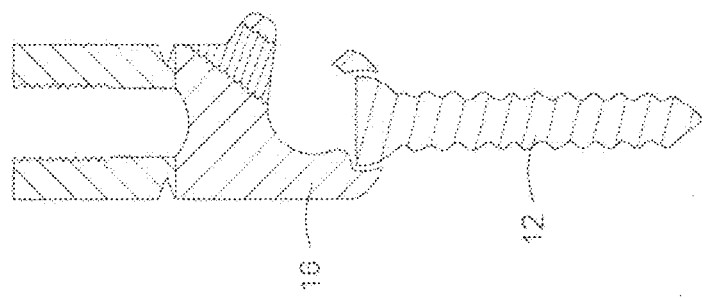
Figure 23:
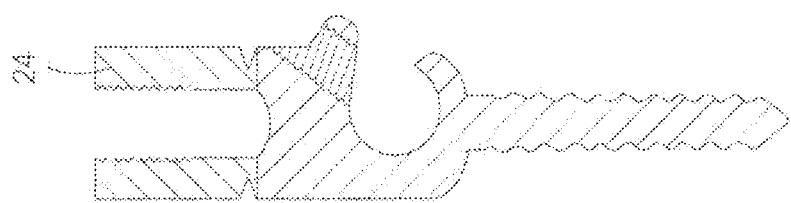
FIG. 23 is an illustration showing the present invention having long upper rod couplings to receive the rod and has a reduction function.
Figure 28:
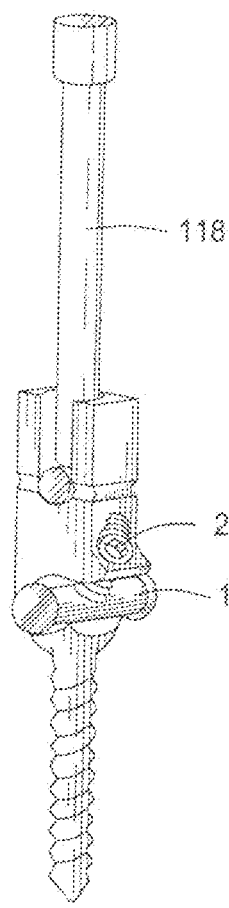
FIGS. 28-29 are pictures illustrating a perspective view of a present invention with a screw driver and a short fixation rod.
Figure 29:
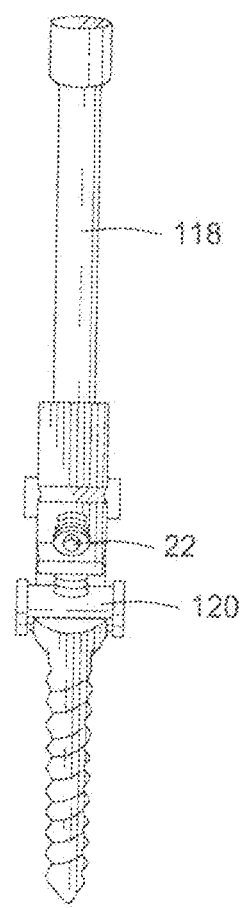

FIG. 23 shows the present invention with extended upper rod coupling 24 that can be reduced or removed if necessary. FIG. 24 shows that the bone fastener 12 is semi-permanently attached to the lower rod coupling 16. FIGS. 24 to 27 show that the bone fastener 12 can be orientated at different angles relative to the rod coupling 16. The angle can vary from any direction and can contain different degrees. For example, the tip of the bone fastener can resemble a circular ball bearing that allows the bone screw to be position in any direction of the x y z plane. FIGS. 28 and 29 show different perspective views of the present invention with a screw driver 118 and a short fixation rod 120. When the short fixation rod 120 is tightened by the rod fastener 22, the pedicle screw 10 is not polyaxial so that the pedicle screw 10 can be inserted by the screw-driver 118. When the rod fastener 22 is loosened, the pedicle screw 10 can polyaxially receive the rod at any direction.

The present invention overcomes the following disadvantages of existing systems, namely, the limitation for the apical vertebral derotation and translation. Another disadvantage or existing systems is the difficulty for concave rod derotation and/or translation which result in pedicle screw loosening with damage to the spinal cord. The present invention overcomes both of these advantages by providing a stable, sturdy platform for use of temporary and permanent rods using a single pedicle screw. The pedicle screw of the present invention maximizes the structural-mechanical properties of each fixation point (the lower versus the upper rod coupling) for each specific type of rod (permanent or temporary) while at the same time maximizing the efficiency of the surgical procedure with less tools and equipment. Furthermore, surgeons are already familiar with similar tools and fasteners and do not have to learn new procedures, techniques or the use of new tools.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Maclennan A. Scoliosis. Br Med J 1922; 2: 865-6.
2. Compere E L. Excision of hemivertebrae for correction of congenital scoliois: report of two cases. JBJS 1932; 14-A; 555-62.
3. Deviten V, Berven S, Smith J A, et al., Excision of hemivertebrae in the management of congenital scoliosis involving the thoracic and thoracolumbar spine. JBJS 2001; 83-B; 496-500.
4. Floman Y, Penny J N, Micheli L J, et al. Osteotomy of the fusion mass in scoliosis. JBJS 1982; 64-A: 1307-16.
5. Luque E R. Vertebral column transposition. Orthop Trans 1983; 7: 29.
6. Leatherman k D, Dickson R A. Two-stage corrective surgery for congenital deformities of the spine. JBJS 1979; 61-B: 324-8.
7. Tokunaga M, Minami S, Kitahara H, et al. Verteral decancellation for severe scoliosis. Spine 2000; 25: 469-74.
8. Wiles P. Resection of dorsalvertebrae in congenital scoliosis. JBJS 1951, 33-A: 151-4.
9. Bradford D S. Vertebral column resection. Orthop Tans 1987; 11: 502.
10. Bradford D S and Boachie-Adjei O. One-stage anterior and posterior hemivertebral resection and arthrodesis for congenital scoliosis. JBJS 1990; 72-A: 536-40.
11. Suk S, Kim J H, Kim W J, et al. Posterior vertebral column resection for severe spinal deformities. Spine 2002; 27 (21): 2374-82.
12. Suk S, Chung E R, Kim J H, et al. Posterior vertebral column resection for severe spinal deformities. Spine 2005; 30 (14): 1682-87.
13. Suk S, Chung E R, Lee S M, et al. Posterior vertebral column resection in fixed lumbosacral deformity. Spine 2005; 30 (23): E703-10.

What is claimed is:

1. A pedicle screw comprising:
a bone fastener and a rod coupling head, the rod coupling head comprising a lower and an upper rod coupling:
the lower rod coupling comprising:
a lateral rod opening adapted to receive a permanent rod, wherein the lateral rod opening is on a side of the pedicle screw;
an angled bore extending into the lateral rod opening along an axis; and
a permanent rod fastener in the angled bore to engage a permanent rod in the lateral rod opening; and
the upper rod coupling comprising:
an upper rod opening adapted to receive a temporary rod, wherein the upper rod opening is formed to receive a temporary rod fastener along an axis which is transverse to the angled bore axis, wherein the upper rod coupling is detachable from the lower rod coupling at a transition; wherein the lateral rod opening is located between the upper rod opening and the bone fastener; and
wherein a temporary rod is temporarily affixed into the upper rod opening during a bone realignment and a permanent rod is positioned in the lateral rod opening and engaged by the permanent rod fastener upon final bone alignment.

2. The screw of claim 1, wherein the lower and upper rod couplings are integral and the transition between the upper and lower rod couplings is breakable.

3. The screw of claim 1, wherein the lower and upper rod couplings are integral and a transition between the upper and lower rod couplings is semi-permanently attached.

4. The screw of claim 1, wherein the transition between the lower and upper rod couplings comprises a universal joint, a pivot, a slot, a collar, a bearing, a dove-tail, a ball-joint, a gimbal, a level, or a sleeve.

5. The screw of claim 1, wherein the lateral and upper rod openings are generally perpendicular.

6. The screw of claim 1, wherein the temporary, the permanent or both fasteners threadably engage the temporary, permanent or both rods.

7. The screw of claim 1, wherein the temporary, the permanent or both fasteners comprise locking pins.

8. The screw of claim 1, wherein the transition between the lower rod coupling and the bone fastener comprises a universal joint, a pivot, a slot, a collar, a bearing, a dove-tail, a ball-joint, a gimbal, a level, or a sleeve.

9. The screw of claim 1, wherein the bone fastener is semi-permanently attached to the rod coupling and allows the rod coupling to be positioned at a variable angle relative to the bone fastener.

10. A method of spinal fixation using pedicle screws comprising:
fastening two or more pedicle screws into two or more vertebra, each pedicle screw comprising a bone fastener and a rod coupling head, the rod coupling head comprising separate lower and upper lower rod couplings:
the lower rod coupling comprising:
a lateral rod opening adapted to receive a permanent rod, wherein the lateral rod opening is on a side of the pedicle screw;
an angled bore extending into the lateral rod opening along an axis; and
a permanent rod fastener in the angled bore to engage a permanent rod in the lateral rod opening; and
the upper rod coupling comprising:
an upper rod opening adapted to receive a temporary rod, wherein the upper rod opening is formed to receive a temporary rod fastener along an axis which is transverse to the angled bore axis; and
wherein the upper rod coupling is detachable from the lower rod coupling at a transition;
interconnecting the pedicle screws with a temporary rod;
correcting a position of the spine by manipulating the temporary rod attached to the pedicle screws;
interconnecting the pedicle screws with a permanent fixation rod; and
removing the temporary rod and the upper rod coupling from the two or more pedicle screws.

11. The method of claim 10, wherein the lower and upper rod couplings are integral and the transition between the upper and lower rod couplings is breakable.

12. The method of claim 10, wherein the lower and upper rod couplings are integral and the transition between the upper and lower rod couplings is semi-permanently attached.

13. The method of claim 10, wherein the transition between the lower and upper rod couplings comprises a universal joint, a pivot, a slot, a collar, a bearing, a dove-tail, a ball-joint, a gimbal, a level, or a sleeve.

14. The method of claim 10, wherein the lateral and upper rod openings are generally perpendicular.

15. The method of claim 10, wherein the temporary, the permanent or both fasteners threadably engage the temporary, permanent or both rods.

16. The method of claim 10, wherein the temporary, the permanent or both fasteners comprise locking pins.

17. The method of claim 10, wherein a transition between the lower rod coupling and the bone fastener comprises a universal joint, a pivot, a slot, a collar, a bearing, a dove-tail, a ball-joint, a gimbal, a level, or a sleeve.

18. The method of claim 10, further comprising using a rod link reducer to perform the step of correcting the spine.

19. The method of claim 10, wherein the bone fastener is semi-permanently attached to the lower rod coupling and allows the lower rod coupling to be positioned at a variable angle relative to the bone fastener.

20. A kit comprising:
two or more pedicle screws, wherein each pedicle screw comprises a bone fastener and a rod coupling head, the rod coupling head comprising separate lower and upper lower rod couplings:
the lower rod coupling comprising:
a lateral rod opening adapted to receive a permanent rod, wherein the lateral rod opening is on a side of the pedicle screw;
an angled bore extending into the lateral rod opening along an axis; and
a permanent rod fastener in the angled bore to engage a permanent rod in the lateral rod opening; and
the upper rod coupling comprising:
an upper rod opening adapted to receive a temporary rod, wherein the upper rod opening is formed to receive a temporary rod fastener along an axis which is transverse to the angled bore axis; wherein the lateral rod opening is located between the upper rod opening and the bone fastener; and
two or more temporary rod fasteners.

21. The kit of claim 20, further comprising a permanent rod and a temporary rod.

22. The kit of claim 20, further comprising one or more rod link reducers.

23. The kit of claim 20, further comprising one or more leverage handles.

24. The kit of claim 20, further comprising two or more permanent rods, two or more temporary rods, one or more rod link reducers and one or more leverage handles.

* * * * *